(12) United States Patent
Alphonse

(10) Patent No.: US 7,327,463 B2
(45) Date of Patent: Feb. 5, 2008

(54) LOW COHERENCE INTERFEROMETRY UTILIZING MAGNITUDE

(75) Inventor: Gerard A. Alphonse, Princeton, NJ (US)

(73) Assignee: Medrikon Corporation, Ewing, NJ (US)

( * ) Notice: Subject to any disclaimer, the term of this patent is extended or adjusted under 35 U.S.C. 154(b) by 153 days.

(21) Appl. No.: 10/845,853

(22) Filed: May 14, 2004

(65) Prior Publication Data

US 2005/0254058 A1 Nov. 17, 2005

(51) Int. Cl.
  G01B 9/02 (2006.01)
  G01B 11/02 (2006.01)
(52) U.S. Cl. .................................. 356/479; 356/497
(58) Field of Classification Search ................ 356/479, 356/497, 477
  See application file for complete search history.

(56) References Cited

U.S. PATENT DOCUMENTS

| | | | |
|---|---|---|---|
| 4,883,953 A | 11/1989 | Koashi | |
| 5,173,747 A | 12/1992 | Boiarski et al. | |
| 5,202,745 A | 4/1993 | Sorin et al. | |
| 5,321,501 A | * 6/1994 | Swanson et al. | ............. 356/479 |
| 5,341,205 A | 8/1994 | McLandrich | |
| 5,383,467 A | 1/1995 | Auer | |
| 5,398,681 A | 3/1995 | Kupershmidt | |
| 5,434,791 A | 7/1995 | Koko | |
| 5,459,570 A | 10/1995 | Swanson | |
| 5,465,147 A | 11/1995 | Swanson | |
| 5,491,552 A | 2/1996 | Knuttel | |
| 5,501,226 A | 3/1996 | Petersen | |
| 5,507,288 A | 4/1996 | Bocker | |
| 5,549,114 A | 8/1996 | Petersen | |
| 5,565,986 A | 10/1996 | Knuttel | |

(Continued)

FOREIGN PATENT DOCUMENTS

EP  0317121 A2  5/1989
EP  0831312 A1  3/1998

(Continued)

OTHER PUBLICATIONS

Joseph M. Schmitt, "Optical Coherence Tomography (OCT): A Review," *IEEE J. Select Topics in Quant. Elect.* vol. 5., No. 4, Jul./Aug. 1999, pp. 1205-1215.

(Continued)

*Primary Examiner*—Patrick Connolly
(74) *Attorney, Agent, or Firm*—Cantor Colburn LLP

(57) ABSTRACT

A method for determining a characteristic of an analyte in a biological sample, the method comprising: directing broadband light by means of a sensing light path at the biological sample, at a target depth defined by the sensing light path and a reference light path; receiving the broadband light reflected from the biological sample by means of the sensing light path; directing the broadband light by means of the reference light path at a fixed reflecting device; and receiving the broadband light reflected from the fixed reflecting device by means of the reference light path. The method also includes interfering the broadband light reflected from the biological sample and the broadband light reflected from the fixed reflecting device; varying an effective light path length of at least one of the reference light path and the sensing light path to define an other target depth; detecting the broadband light resulting from interference of the broadband light reflected from the biological sample and the broadband light reflected from the fixed reflecting device for each of the target depths, to provide an intensity measurement at each of the target depths; and determining the characteristic of the analyte in the biological sample from variations in the intensity measurements.

36 Claims, 16 Drawing Sheets

U.S. PATENT DOCUMENTS

| | | |
|---|---|---|
| 5,582,171 A | 12/1996 | Chornenky |
| 5,710,630 A | 1/1998 | Essenpreis |
| 5,726,801 A | 3/1998 | Pan |
| 5,830,145 A | 11/1998 | Tenhoff |
| 5,835,215 A | 11/1998 | Toida |
| 5,835,642 A | 11/1998 | Gelikonov |
| 5,836,877 A | 11/1998 | Zavislan |
| 5,847,827 A | 12/1998 | Fercher |
| 5,867,268 A | 2/1999 | Gelikonov |
| 5,877,856 A | 3/1999 | Fercher |
| 5,883,717 A | 3/1999 | DiMarzio |
| 5,892,583 A | 4/1999 | Li |
| 5,905,572 A | 5/1999 | Li |
| 5,920,390 A | 7/1999 | Farahi |
| 5,921,926 A | 7/1999 | Rolland |
| 5,943,133 A | 8/1999 | Zeylikovich |
| 5,956,355 A | 9/1999 | Swanson |
| 5,962,852 A | 10/1999 | Knuettel |
| 5,991,697 A | 11/1999 | Nelson |
| 5,994,690 A | 11/1999 | Kulkarni |
| 6,002,480 A | 12/1999 | Izatt |
| 6,006,128 A | 12/1999 | Izatt |
| 6,014,214 A | 1/2000 | Li |
| 6,015,969 A | 1/2000 | Nathel et al. |
| 6,020,963 A | 2/2000 | DiMarzio |
| 6,037,579 A | 3/2000 | Chan |
| 6,053,613 A | 4/2000 | Wei |
| 6,057,920 A | 5/2000 | Fercher |
| 6,069,698 A | 5/2000 | Ozawa |
| 6,072,765 A | 6/2000 | Rolland |
| 6,111,645 A | 8/2000 | Tearney |
| 6,124,930 A | 9/2000 | Fercher |
| 6,134,003 A * | 10/2000 | Tearney et al. ............ 356/479 |
| 6,141,577 A | 10/2000 | Rolland |
| 6,144,449 A | 11/2000 | Knuettel |
| 6,152,875 A | 11/2000 | Hakamata |
| 6,160,826 A | 12/2000 | Swanson |
| 6,175,669 B1 | 1/2001 | Colston |
| 6,191,862 B1 | 2/2001 | Swanson |
| 6,198,540 B1 | 3/2001 | Ueda |
| 6,201,608 B1 | 3/2001 | Mandella |
| 6,208,415 B1 | 3/2001 | De Boer |
| 6,219,055 B1 | 4/2001 | Bhargava |
| 6,226,089 B1 | 5/2001 | Hakamata |
| 6,233,055 B1 | 5/2001 | Mandella |
| 6,252,666 B1 * | 6/2001 | Mandella et al. .......... 356/479 |
| 6,268,921 B1 | 7/2001 | Seitz |
| 6,282,011 B1 | 8/2001 | Tearney |
| 6,288,784 B1 | 9/2001 | Hitzenberger |
| 6,304,373 B1 | 10/2001 | Zavislan |
| 6,307,633 B1 | 10/2001 | Mandella |
| 6,307,634 B2 | 10/2001 | Hitzenberger |
| 6,330,063 B1 | 12/2001 | Knuettel |
| 6,351,325 B1 | 2/2002 | Mandella |
| 6,370,422 B1 | 4/2002 | Richards-Kortum |
| 6,377,349 B1 | 4/2002 | Fercher |
| 6,381,015 B1 | 4/2002 | Sonehara |
| 6,381,025 B1 | 4/2002 | Bornhop |
| 6,381,490 B1 | 4/2002 | Ostrovsky |
| 6,384,915 B1 | 5/2002 | Everett |
| 6,385,358 B1 | 5/2002 | Everett |
| 6,390,978 B1 | 5/2002 | Irion |
| 6,407,872 B1 | 6/2002 | Lai |
| 6,419,360 B1 | 7/2002 | Hauger |
| 6,421,164 B2 | 7/2002 | Tearney |
| 6,423,956 B1 | 7/2002 | Mandella |
| 6,430,455 B1 | 8/2002 | Rebello |
| 6,437,867 B2 | 8/2002 | Zeylikovich |
| 6,441,356 B1 | 8/2002 | Mandella |
| 6,445,939 B1 | 9/2002 | Swanson |
| 6,445,944 B1 | 9/2002 | Ostrovsky |
| 6,456,769 B1 | 9/2002 | Furusawa |
| 6,466,713 B2 | 10/2002 | Everett |
| 6,469,489 B1 | 10/2002 | Bourquin |
| 6,477,403 B1 | 11/2002 | Eguchi |
| 6,485,413 B1 | 11/2002 | Boppart |
| 6,496,267 B1 | 12/2002 | Takaoka |
| 6,498,948 B1 | 12/2002 | Ozawa |
| 6,501,551 B1 | 12/2002 | Tearney |
| 6,507,747 B1 | 1/2003 | Gowda |
| 6,519,076 B2 | 2/2003 | Fisher |
| 6,522,913 B2 | 2/2003 | Swanson |
| 6,525,862 B2 | 2/2003 | Fisher |
| 6,527,708 B1 | 3/2003 | Nakamura |
| 6,538,817 B1 | 3/2003 | Farmer |
| 6,546,272 B1 | 4/2003 | MacKinnon |
| 6,549,801 B1 | 4/2003 | Chen |
| 6,552,796 B2 | 4/2003 | Magnin |
| 6,564,087 B1 | 5/2003 | Pitris |
| 6,564,089 B2 | 5/2003 | Izatt |
| 6,570,659 B2 | 5/2003 | Schmitt |
| 6,571,117 B1 | 5/2003 | Marbach |
| 6,577,394 B1 | 6/2003 | Zavislan |
| 6,615,071 B1 | 9/2003 | Casscells |
| 6,701,181 B2 | 3/2004 | Tang et al. |
| 7,184,148 B2 * | 2/2007 | Alphonse ............... 356/479 |
| 7,242,480 B2 * | 7/2007 | Alphonse ............... 356/479 |
| 2001/0047137 A1 | 11/2001 | Moreno |
| 2003/0023152 A1 | 1/2003 | Abbink |
| 2003/0023170 A1 | 1/2003 | Gardner et al. |
| 2003/0028100 A1 | 2/2003 | Tearney |
| 2003/0055307 A1 | 3/2003 | Elmaleh |
| 2003/0076508 A1 | 4/2003 | Cornsweet |
| 2003/0112444 A1 | 6/2003 | Yang et al. |
| 2003/0137669 A1 | 7/2003 | Rollins |
| 2003/0171691 A1 | 9/2003 | Casscella |
| 2005/0004453 A1 | 1/2005 | Tearney et al. |

FOREIGN PATENT DOCUMENTS

| | | |
|---|---|---|
| EP | 0831312 B1 | 10/2001 |
| WO | WO 92/19930 | 4/1992 |
| WO | WO 97/32182 | 9/1997 |
| WO | WO9932897 A2 | 12/1997 |
| WO | WO9957507 A1 | 4/1998 |
| WO | WO0112060 A2 | 8/2000 |
| WO | WO0280767 A1 | 3/2002 |
| WO | WO03010510 A2 | 7/2002 |
| WO | WO03088817 A2 | 10/2003 |
| WO | WO2005/114094 A1 | 12/2005 |

OTHER PUBLICATIONS

Gerard A. Alphonse, "Design of High-Power Superluminescent Diodes with Low Spectral Modulation," *Proceedings of SPIE*, vol. 4648, pp. 125-138 (2002).

Andrew M. Rollins and Joseph A. Izatt, "Optical Interferometer Designs for Optical Coherence Tomography," *Optics Lett.* vol. 24, No. 21, Nov. 1, 1999, pp. 1484-1486.

Rinat O. Esenaliev, Kirill V. Larin and Irina V. Larina, "Noninvasive Monitoring of Glucose Concentration with Optical Coherence Tomography," *Optics Lett.* vol. 28, No. 13, Jul. 1, 2001, pp. 992-994.

Kirill V. Larin, Moshen S. Eledrisi, Massoud Motemedi, and Rinat O. Esenaliev, "Noninvasive Blood Glucose Monitoring with Optical Coherence Tomography—A Pilot Study in the Human Subjects," *Diabetes Care*, vol. 25, No. 12, Dec. 2002, pp. 2263-2267.

H.C. Casey, Jr. and M.B. Panish, *Heterostructure Lasers Parts A and B*, Academic Press, New York, 1978. pp. 207-217.

R.W. Waynant, V.M. Chenault, Overview of Non-Invasive Fluid Glucose Measurement Using Optical Techniques to Maintain Glucose Control in Diabetes Mellitus, *LEOS Newsletter*, vol. 12, No. 2, Apr. 1998.

R.J. McNichols, G.L. Cote, Optical Glucose Sensing in Biological Fluids: An Overview, Journal of Biomedical Optics, vol. 5, 2000, pp. 5.

A. Dogariu and G. Popescu, "High-Resolutionspatial and Spectral Characterization of Optical Fields," *Optics & Photonics News*, Dec. 2002, p. 21.

M. Kohl, M. Cope, M. Essenpries, D. Bocker, "Influence of Glucose Concentration on Light Scattering in Tissue-Simulating Phantoms," *Optics Letters*, vol. 19, No. 2, Dec. 15, 1994, pp. 2170.

J. T. Bruulsema, et al, "Correlation Between Blood Glucose Concentration in Diabetics and Noninvasively Measured Tissue Optical Scattering Coefficient," *Optics Letters*, vol. 22, No. 3, Feb. 1, 1997, pp. 190.

J. M. Schmidt, S.H. Xiang, K.M.Yung, "Speckle in Optical Coherence Tomography" *J. of Biomedical Optics*, vol. 4, No. 1, Jan. 1999, pp. 95-105.

A. M. Rollins, J.A. Izatt, Optimal Interferometer Designs for Optical Coherence Tomography, *Optics Letters*, vol. 24 (21), Nov. 1, 1999, pp. 1484.

S.L. Jacques, Skin Optics, Oregon Medical Laser Center News, Jan. 1998.

J. M. Schmitt, G. Kumar, Optical Scattering Properties of Soft Tissue: A Discrete Particle Model, *Applied Optics*, vol. 37, No. 13, May 1, 1998, pp. 2788.

Aristide Dogariu and Gabriel Popsecu, "Measuring the Phase of Spatially Coherent Polychromatic Fields," School of Optics, University of Central Florida, vol. 89, No. 24, Dec. 9, 2002, pp. 1-2.

John S. Maier et al., "In Vivo Study of Human Tissues with a Portable Near-Infrared Tissue Spectrometer," http://lfd.uiuc.edu/spie95/jm/jmspie95.html, pp. 1-8. (1995).

Valery V. Tuchin, "Light Propagation in Tissues with Controlled Optical Properties," *J. Biomedical Optics* 2(04), 1997, pp. 401-417.

Kirill V. Larin, Massoud Motamedi, Taras V. Ashitkov, and Rinat O. Esenaliev, "Specificity of Noninvasive Blood Glucose Sensing Using Optical Coherence Tomography Technique: A Pilot Study," Physics in Medicine and Biology, Phys. Med. Biol. 48 (2003) pp. 1371-1390.

Akira Ishimaru, "Diffusion of Light in Turbid Material," *Applied Optics*, vol. 28, No. 12, Jun. 15, 1989, pp. 2210-2215.

Sid Bennett and Steven R. Emge, "Fiber Optic Rate Gyro for Land Navigation and Platform Stabilization," Sensors Exp 1994, Cleveland, Ohio, Sep. 20, 1994.

A F. Fercher, K. Mengedoht, and W. Werner, "Eye-Length Measurement By Interferometry with Partially Coherent Light," *Optic Letters*, Optical Society of America, vol. 13 No. 3, Mar. 1988, pp. 186-188.

B.L. Danielson and C.D. Whittenberg, "Guided-wave Reflectometry with Micrometer Resolution," *Applied Optics*, vol. 26, No. 14, Jul. 15, 1987.

Kazumasa Takada, Itaru Yokohama, Kazumori Chida, and Juichi Noda, "New Measurement System for Fault Location in Optical Waveguide Devices Based on an Interferometric Technique," *Applied Optics*, vol. 26, No. 9., May 1, 1987, pp. 1603-1606.

Robert C. Youngquist, Sally Carr and D.E.N. Davies, Optical Coherence-Domain Reflectometry: A New Optical Evaluation Technique, *Optics Letters*, vol. 12, No. 3, Mar. 1987.

Harry Delcher, "Continuous Measurement of Glucose in Interstitial Fluid for Extended Time Periods," SpectRx Inc., pp. 1-8, (2000).

PCT International Search Report PCT/US2005/015373 Apr. 5, 2005.

PCT International Search Report PCT/US2005/015558 Apr. 5, 2005.

PCT International Search Report PCT/US2005/015372 Apr. 5, 2005.

Optical Coherence tomography—principles and applications, by A.F. Fercher, W. Drexler, C.K. Hitzenberger and T. Lasser, Institute of Physics Publishing, Reports on Progress in Physics, Jan. 20, 2003, pp. 239-303.

Low Coherence Interferometric Fibre Multiplexed Sensor Systems Using an Integrated-Optical Configuration, by A.J. Rogers, M.J. Plissi, Department of Electronic and Electrical Engineering, King's College London, UK Spie vol. 2510 XP-002112588, (1995).

Integrated Optic Error Detecting Circuit Using Ti:Linbo3 Interferometric Light Modulators by Hiroshi Haga, Masato Ohta, Masayuki Izutsu and Tadasi Sueta Faculty of Engineering Science, Osaka University Toyonaka, Osaka 560, Japan IOOOC-ECOC '85, (1985).

Recent progress in fibre optic low-coherence interferometry by Yun-Jiang Rao and David A. Jackson Applied Optics Group, Physics Dept., University of Kent at Canterbury, Kent CT2 7NR, UK Meas. Sci. Technol. 7 (1996) pp. 981-999.

International Search Report, PCT/US2004/042643, May 20, 2005.

PCT International Search Report/US2006/002244.

G. Popescu, C. Mjufat, A. Dogariu, Evidence of Scattering Anisotropy Effects on Boundary Conditions of the Diffusion Equation; Phys. Rev. E; Eol. 61; 2000; pp. 4523-4529.

A. Smith, D. Yang, H. Delcher,. J. Eppstein, D. Williams, and S. Wilkes, Fluorescein kinetics in Interstitial Fluid Harvested from Diabetic Skin During Fluorescein Angiography: Implications for Glucose Monitoring; Diabetes Technology & Therapeutics vol. 1(1); 1999; pp. 21-27.

G. Popescu, and A. Dogariu, Optical Path-Length Spectroscopy of Wave Propagation in Random Media; Optics Letters; vol. 24(7); Apr. 1, 1999; pp. 442-444.

A. Dunn and . R. Richards-Kortum, Three-dimensional Computation of Light Scattering from Cells; IEEE Journal of Selected Topics in Quantum Electronics; vol. 2; No. 4; Dec. 1996.

F. A. Duck, Physical Properties of Tissue; Academic; Longon; 1990.

W.F. Cheong, S.A. Prahl, and A.J. Welsh, A Review of the Optical Properties of Biological Tissues; IEEE Journal of Quantum Electronics; vol. 26; 1990; pp. 2166-2185.

M.J. C. van Gernert, S.L. Jacques, H.J.C.M. Sterenbord, and W.M. Star, Skin Optics; IEEE Transactions on Biomedical Engineering; vol. 36(12); 1989; 99. 1146-1154.

J.J. Duderstadt, and L. J. Hamilton, Nuclear Reactor Analysis; Wiley; New York; 1976; pp. 133-138.

D.J. Durian, Influence of the Boundary Reflection and Refraction on Diffusive Photon Transport; Phys. Rev. E; vol. 50; 1994; pp. 442-444.

J.X. Zhu, D.J. Pine, and D.A. Weitz, Internal Reflection of Diffusive Light in Random Media; Physical Review A; vol. 44; 1991; pp. 3948-3959.

M.S. Patterson, B. Chance, and B.C. Wilson, Time Resolved Reflectance and Transmittance for the Non-invasive Measurement of Tissue Optical Properties; Applied Optics; vol. 28(12); 1989; pp. 2331-2336.

V. N. Vapnik, Statistical Learning Theory; John Wiley & Sons, 1998, pp. 19-51.

W.H. Press et al, Numerical Recipes in C: the Art of Scientific Computing; 2nd Edition; Cambridge University Press; 1992; pp. 394-455.

V. Cherassky; and F. Mulier, Learning from Data; John Wiley & Sons; 1998; pp. 17-21; 38-41; 54; 122.

V. Cherassky, Model Complexity Control and Statistical Learning Theory; Natural Computing; Kluwer; vol. 1; No.; 2002; pp. 1-19.

Aryan Vink, Atherosclerotic Plaques: How Vulnerable is the Definition of "the Vulnerable Plaque"? Journal of Interventional Cardiology, vol. 16, No. 2, 2003, pp. 115-122.

Renu Virami, M.D., "Pathology of the Thin-Cap Fibroatheroma: A Type of Vulnerable Plaque," Journal of Interventional Cardiology, vol. 16, No. 3, 2003, pp. 267-272.

Morteza Naghavi MD, "From Vulnerable Plaque to Vulnerable Patient," Circulation, Oct. 7, 2003, pp. 1664-1672.

Renu Virami, "Lessons from Sudden Coronary Death," Arterioscler Thromb Biol., May 2000, pp. 1262-1275.

* cited by examiner

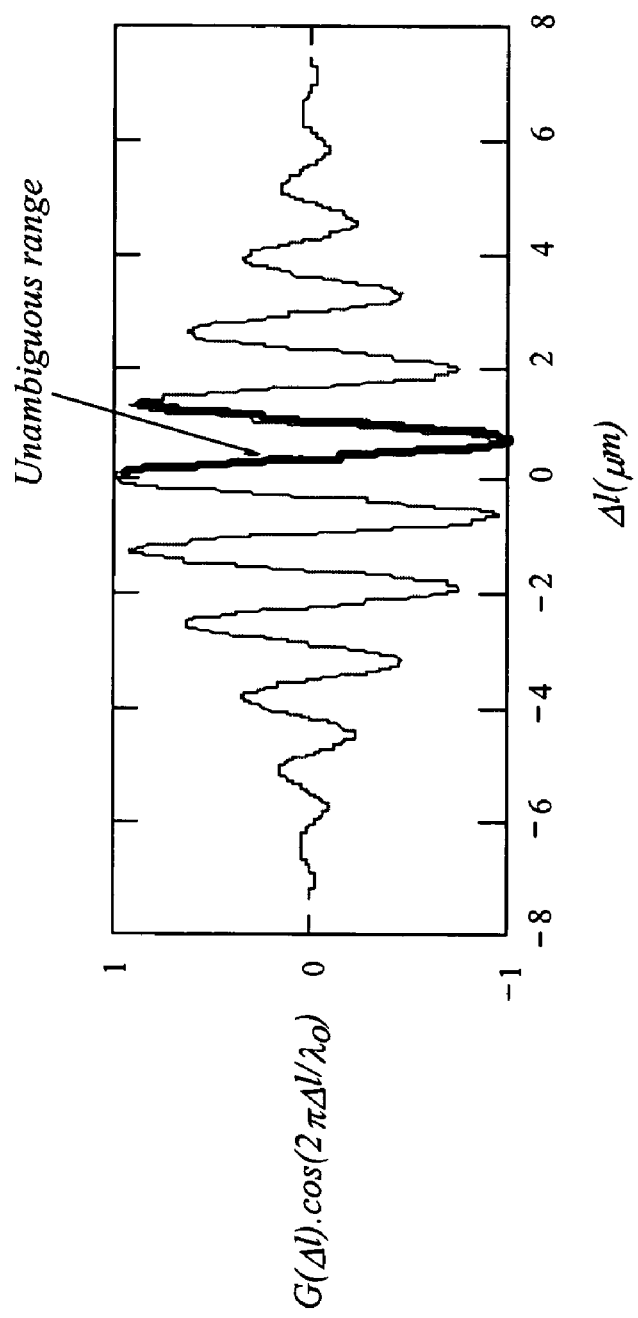

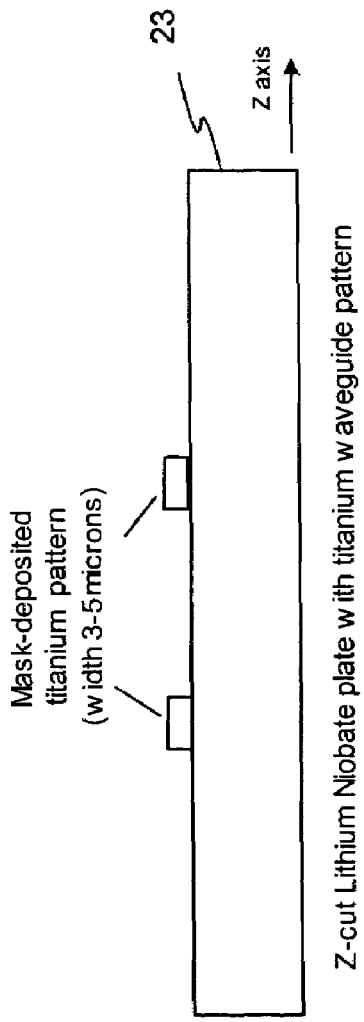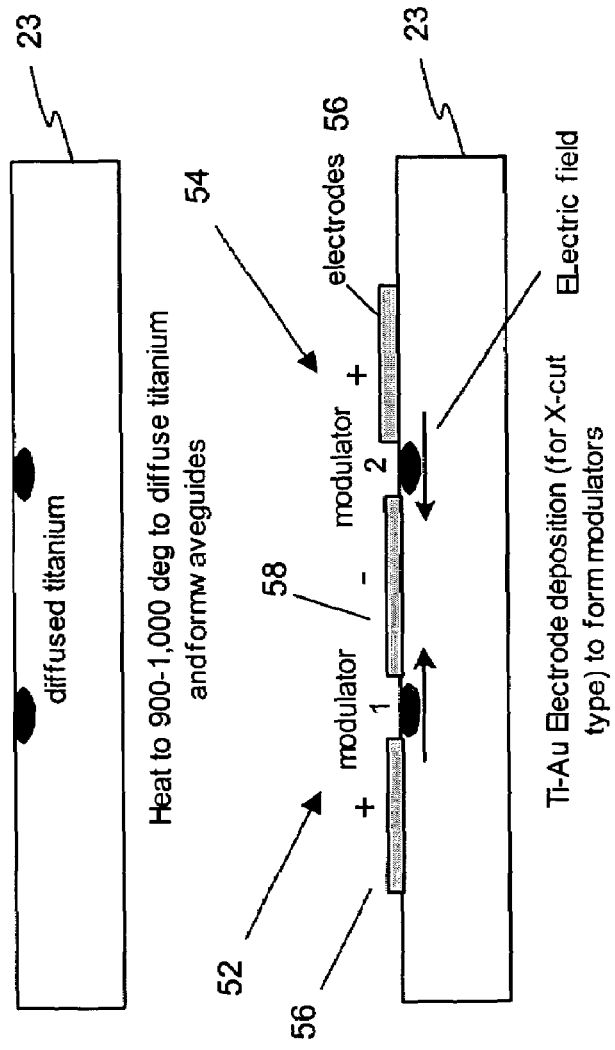

LOW COHERENCE INTERFEROMETRY UTILIZING MAGNITUDE

BACKGROUND

The invention concerns a method for low coherence interferometry of a biological sample using magnitude. The term "biological sample" denotes a body fluid or tissue of an organism. Biological samples are generally optically heterogeneous, that is, they contain a plurality of scattering centers scattering irradiated light. In the case of biological tissue, especially skin tissue, the cell walls and other intra-tissue components form the scattering centers.

Generally, for the qualitative and quantitative analysis in such biological samples, reagents or systems of reagents are used that chemically react with the particular component(s) to be determined. The reaction results in a physically detectable change in the solution of reaction, for instance a change in its color, which can be measured as a measurement quantity. By calibrating with standard samples of known concentration, a correlation is determined between the values of the measurement quantity measured at different concentrations and the particular concentration. These procedures allow accurate and sensitive analyses, but on the other hand they require removing a liquid sample, especially a blood sample, from the body for the analysis ("invasive analysis").

The American Diabetes Association (ADA) estimates that diabetes afflicts nearly 17 million people in the United States. Diabetes can lead to severe complications over time, including heart failure, kidney failure, blindness, and loss of limb due to poor peripheral circulation. According to ADA, complications arising from diabetes cost the U.S. health care system in excess of $132 Billion.

Diabetes complications are largely due to years of poor blood glucose control. The Diabetes Care and Complications Trial (DCCT) carried out by the National Institute of Diabetes and Digestive and Kidney Diseases (NIDDK) demonstrated that more frequent monitoring of blood glucose and insulin levels can prevent many of the long-term complications of diabetes.

Monitoring of blood glucose concentration is key to managing the therapy of diabetes patients. Monitoring results are used to adjust nutrition, medication, and exercise in order to achieve the best possible glucose control, reducing the complications and mortality associated with diabetes. At present, the most widely used method for monitoring of blood glucose by diabetes patients involves chemical analysis of blood samples taken by puncturing the finger or forearm. This method is painful, requires relatively complex operations, is inconvenient due to disruption of daily life, and may become difficult to perform in the long term due to calluses on the fingers and poor circulation. As a result, the average diabetic patient tests his/her blood glucose levels less than twice a day versus the recommended four or more times per day. Non-invasive blood glucose monitoring techniques with accuracies equal to or better than the current chemical glucose methods are therefore needed.

Accordingly, a number of procedures and apparatus have been suggested to determine glucose in blood, tissue and other biological samples in vivo and in a non-invasive manner. Existing non-invasive procedures for glucose determination include nuclear magnetic resonance (NMR), electron spin resonance (ESR) and infrared spectroscopy. However, none of these procedures has achieved practical significance. Large and costly equipment is required, which are wholly unsuitable for routine analysis or even for patient self-checking (home monitoring).

One of the most promising approaches for non-invasive glucose monitoring is based on optical techniques. Optical glucose monitoring techniques are particularly attractive in that they are relatively fast, use non-ionizing radiation, and generally do not require consumable reagents. Several optical glucose monitoring techniques have been proposed so far, with varying degrees of success. Several of these techniques are discussed herein as background, however, once again, none of these techniques has attained significant commercial success relative to invasive techniques.

One approach is Near-Infrared (NIR)/Mid-Infrared (MIR) spectroscopy. In infrared spectroscopy, radiation from external light sources is transmitted through or reflected by a body part. Spectroscopic techniques are used to analyze the amount of radiation absorbed at each wavelength by the body part constituents and to compare the absorption data to known data for glucose. Practical implementation of a glucose sensor based on these principles is very difficult and several wavelengths are required. Infrared (IR) spectra are sensitive to physical and chemical factors such as temperature, pH, and scattering. Furthermore, spectroscopy is affected by skin pigmentation, use of medications that absorb various IR wavelengths, alterations in blood levels of hemoglobin or other proteins that absorb IR, changes in body temperature, and alterations in the state of hydration or nutrition. In addition, the NIR spectrum of glucose is very similar to that of other sugars, including fructose, which is often used by diabetics. Therefore, the signal (i.e. the change in the absorption spectrum as a function of glucose concentration) is very small compared to noise and to interference resulting especially from the water spectral absorption and other strongly absorbing components.

Another approach is Raman Spectroscopy. With Raman spectroscopy, Raman spectra are observed when incident radiation is inelastically scattered. The loss or gain of photon energy are independent of the excitation frequency and provide specific information about the chemical structure of the sample. The Raman signal is very weak, requiring long data acquisition time, making the device sensitive to light source fluctuations. Measurements are subject to high background noise because of tissue autofluorescence. Scatter and reabsorption in biological tissues make detection of Raman frequency shifts due to physiological concentrations difficult.

Another spectroscopic approach is based on photoacoustics. In photoacoustic spectroscopy, a laser beam pulse is used to rapidly heat the tissue and generate an acoustic pressure wave that can be measured by a microphone or other transducer. The acoustic signal is analyzed to infer blood glucose concentration. Measurements are affected by chemical interferences from biological molecules as well as physical interference from temperature and pressure changes. Current instruments are complex and sensitive to environmental conditions.

Another optical approach considered of glucose monitoring is based on employing polarimetry. Glucose concentration changes the polarization of light fields. The eye's aqueous humor has been suggested as the medium for this technique as skin is not a feasible site due to its high light scattering properties. However, polarization measurements are affected by optical rotation due to cornea, and by other optically active substances. Other interfering factors include saccadic motion and corneal birefringence. In addition, there is a significant lag between blood glucose changes and glucose changes in intra-ocular fluids, of up to 30 minutes.

Yet, another approach employed for glucose monitoring is based on light scattering. Changes in glucose levels induce changes in light scattering properties, generally, of the skin. U.S. Pat. No. 6,226,089 to Hakamata discloses detecting the intensities of backscattering light generated by predetermined interfaces of an eyeball when a laser beam emitted from a semiconductor laser is projected onto the eyeball in a predetermined position. The absorbance or refractive index of the aqueous humor in the anterior chamber of the eyeball is determined on the basis of the intensities of the backscattering light, and the glucose concentration in the aqueous humor is determined on the basis of the absorbance or refractive index in the aqueous humor. Light scattering effects are evident in the near-infrared range, where water absorption is much weaker than at larger wavelengths (medium- and far-infrared). However, techniques that rely on the backscattered light from the aqueous humor of the eye are affected by optical rotation due to cornea, and by other optically active substances. Other interfering factors include saccadic motion and corneal birefringence. Finally, it should be appreciated that there is often a significant time lag, (e.g., up to 30 minutes) between blood glucose changes and glucose changes of the intra-ocular fluids.

Low-Coherence Interferometry (LCI) is one technique for analyzing skin light scattering properties. Low Coherence Interferometry (LCI) is an optical technique that allows for accurate, analysis of the scattering properties of heterogeneous optical media such as biological tissue. In LCI, light from a broad bandwidth light source is first split into sample and reference light beams which are both retro-reflected, from a targeted region of the sample and from a reference mirror, respectively, and are subsequently recombined to generate an interference signal. Constructive interference between the sample and reference beams occurs only if the optical path difference between them is less than the coherence length of the source.

U.S. Pat. No. 5,710,630 to Essenpreis et al. describes a glucose measuring apparatus for the analytical determination of the glucose concentration in a biological sample and comprising a light source to generate the measuring light, light irradiation means comprising a light aperture by means of which the measuring light is irradiated into the biological sample through a boundary surface thereof, a primary-side measuring light path from the light source to the boundary surface, light receiving means for the measuring light emerging from a sample boundary surface following interaction with said sample, and a secondary-side sample light path linking the boundary surface where the measuring light emerges from the sample with a photodetector. The apparatus being characterized in that the light source and the photodetector are connected by a reference light path of defined optical length and in that an optic coupler is inserted into the secondary-side measurement light path which combines the secondary-side measuring light path with the reference light path in such manner that they impinge on the photodetector at the same location thereby generating an interference signal. A glucose concentration is determined utilizing the optical path length of the secondary-side measuring light path inside the sample derived from the interference signal.

BRIEF SUMMARY

The above-discussed and other drawbacks and deficiencies of the prior art are overcome or alleviated by the measurement system and methodology disclosed herein. Disclosed herein in an exemplary embodiment is a method for determining a characteristic of an analyte in a biological sample, the method comprising: directing broadband light by means of a sensing light path at the biological sample, at a target depth defined by the sensing light path and a reference light path; receiving the broadband light reflected from the biological sample by means of the sensing light path; directing the broadband light by means of the reference light path at a fixed reflecting device; and receiving the broadband light reflected from the fixed reflecting device by means of the reference light path. The method also includes interfering the broadband light reflected from the biological sample and the broadband light reflected from the fixed reflecting device; varying an effective light path length of at least one of the reference light path and the sensing light path to define an other target depth; detecting the broadband light resulting from interference of the broadband light reflected from the biological sample and the broadband light reflected from the fixed reflecting device for each of the target depths, to provide an intensity measurement at each of the target depths; and determining the characteristic of the analyte in the biological sample from variations in the intensity measurements.

Disclosed herein in another exemplary embodiment is a system for determining a characteristic of an analyte in a biological sample, the system comprising: a broadband light source for providing a broadband light; and a sensing light path receptive to the broadband light from the broadband light source. The sensing light path is configured to direct the broadband light at the biological sample and to receive the broadband light reflected from the biological sample. The system also comprising: a fixed reflecting device and a reference light path receptive to the broadband light from the broadband light source. The reference light path is configured to direct the broadband light at the fixed reflecting device and to receive the broadband light reflected from the fixed reflecting device. The reference light path is coupled with the sensing light path to facilitate interference of the broadband light reflected from the biological sample and the broadband light reflected from the fixed reflecting device. The reference light path and the sensing light path cooperating to define a target depth. The system further includes a means for varying an effective light path length of at least one of the reference light path and the sensing light path to define an other target depth; a detector receptive to the broadband light resulting from interference of the broadband light reflected from the biological sample and the broadband light reflected from the fixed reflecting device for each of the target depths, to provide an intensity measurement at each of the target depths; and a processing means configured to determine the characteristic of the analyte in the biological sample from variations in the intensity measurements.

BRIEF DESCRIPTION OF THE DRAWINGS

These and other features and advantages of the present invention may be best understood by reading the accompanying detailed description of the exemplary embodiments while referring to the accompanying figures wherein like elements are numbered alike in the several figures in which:

FIG. 3 depicts a range of unambiguous measurement for a periodic interference signal;

FIG. 10A depicts a process for fabricating the splitter-modulator module in accordance with an exemplary embodiment;

FIG. 10B depicts a process of fabricating the splitter-modulator module in accordance with an exemplary embodiment;

FIG. 10C depicts a process of fabricating the splitter-modulator module in accordance with an exemplary embodiment;

DETAILED DESCRIPTION OF AN EXEMPLARY EMBODIMENT

Figure 1:
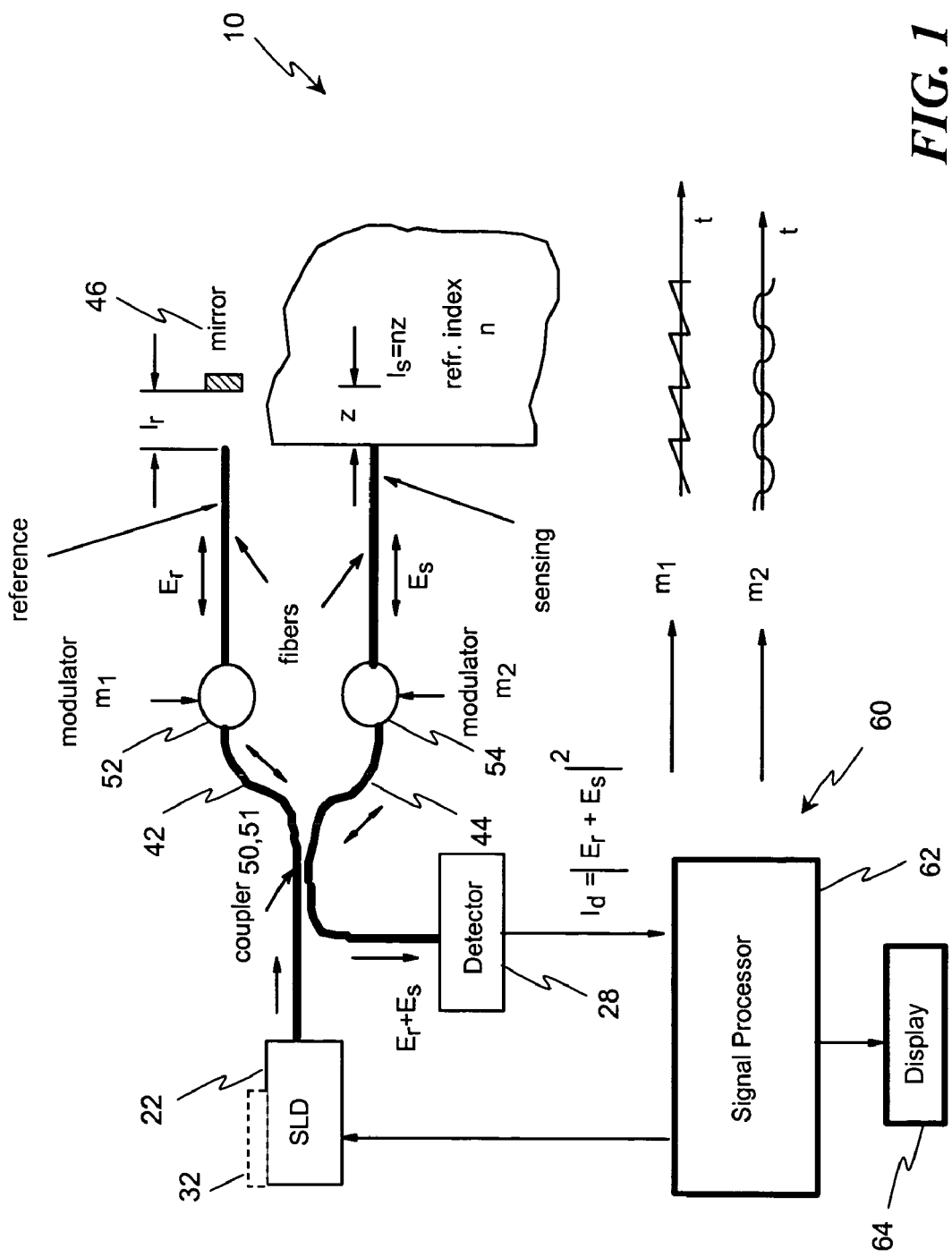
FIG. 1 is a basic all-fiber low-coherence interferometer (LCI)

Disclosed herein, in several exemplary embodiments are high-sensitivity low coherence interferometric (LCI) systems (instruments) for optical metrology, which in an exemplary embodiment are miniaturized for use in a variety of sensing and monitoring applications, including, but not limited to, trace chemical sensing, optical properties and changes thereof, medical sensing such as non-invasive glucose monitoring and others. In an exemplary embodiment, the instrument is miniaturized, using integrated optics components such as waveguides, splitters and modulators on a single substrate such as, but not limited to, a LiNbO3 (Lithium Niobate) chip. The exemplary embodiments may also involve the use of a "circulator" type of optical component, including of a polarizing beam splitter and quarter-wave plate, which can be combined with the light source and detector into a miniature module that prevents optical feedback into the light source while doubling the detected light. Alternatively, instead of the polarizing beam splitter and quarter wave plate one or more isolators and a waveguide coupler may be employed in a similar module to accomplish the same purpose. Disclosed herein in the exemplary embodiments are multiple methodologies and associated systems employed to derive information from the magnitude and/or phase of an interferometric signal.

It will be appreciated that while the exemplary embodiments described herein are suitable for the analysis in comparatively highly scattering, i.e. optically heterogeneous biological samples, optically homogeneous (that is, low-scattering or entirely non-scattering) samples also may be analyzed provided suitable implementations of the embodiments of the invention are employed. It may be further appreciated that the methods discussed herein generally do not allow an absolute measurement of the glucose concentration, but rather a relative measurement from a given baseline. Therefore, calibration to establish a baseline is required. For instance, for one exemplary embodiment, a calibration strip is employed to facilitate calibration. Other methodologies, such as using a sample of known index of refraction, or known glucose concentration may also be employed. The particular glucose concentration in the sample may be determined by any previously known procedure, which allows the determination of the absolute glucose concentration.

It should noted that the light wavelengths discussed below for such methods are in the range of about 300 to about several thousand nanometers (nm), that is in the spectral range from near ultraviolet to near infrared light. In an exemplary embodiment, for the sake of illustration, a wavelength of about 1300 nm is employed. The term "light" as used herein is not to be construed as being limited or restricted to the visible spectral range.

It is well known that the presence of glucose affects the light scattering properties of tissue, and the refractive index denoted as n of the Interstitial Fluid (ISF) and the refractive index of the scattering centers in the tissue—cell membranes, cellular components and protein aggregates. It is also known that a near infrared (NIR) light of a few milliwatts optical power can penetrate the skin harmlessly, whether being delivered directly from the air, a fiber, some appropriate waveguide, or some combination thereof. In the NIR range the refractive index of ISF is about 1.348-1.352, whereas the refractive index of cellular membranes and protein aggregates ranges from about 1.350 to 1.460. Since the tissue under the skin is highly scattering, the light is scattered in all directions, and only a small amount, the so-called ballistic photons, is captured. It is the light from the ballistic photons captured that are employed to produce an interferometric signal. Raising the glucose concentration in the ISF raises the ISF refractive index by approximately $1.52 \times 10^{-6}$ per each mg/dl. Furthermore, the physiological delay of blood glucose transfer from blood to the ISF is of the order of only 2-5 minutes, which makes monitoring of blood glucose in ISF highly practical especially compared to existing methodologies that employ the aqueous humor of the eye.

It will also be noted that for a homogeneously scattering medium for which a specific property such as the refractive index is to be measured, it is sufficient to probe at a single depth, as the desired information can be obtained from the phase of the interferometric signal, presumed to be independent of the amplitude. In this case, an instrument as described herein can be configured for measurement at a single depth. However, if desired, to probe for inhomogeneities (local changes of absorption, reflection, or refractive index), the instrument may be configured to measure both the amplitude and the phase of the interferometric signal as functions of depth. Described herein in a first exemplary embodiment is a system configured to probe at a fixed depth, while later embodiments may be employed for measurement at variable depths and for general imaging purposes. In any case, emphasis is placed on miniaturization, portability, low power and low cost.

Finally, it will also be appreciated that while the exemplary embodiments disclosed herein are described with reference and illustration to glucose measurements, applications and implementations for determination of other characteristics of analytes may be understood as being within the scope and breadth of the claims. Furthermore, the methodology and apparatus of several exemplary embodiments are also non-invasive, and thereby eliminate the difficulties associated with existing invasive techniques. In particular, with respect to detection of glucose concentration, the LCI systems of several exemplary embodiments are configured to be non-invasive, avoiding painful lancets and the like.

Another important consideration is that, as a tool, particularly for medical diagnostic applications, the LCI system of the exemplary embodiments is preferably configured to be easily portable, and for use by outpatients it must be small. Once again, for the purpose of illustration, the LCI system 10 will be described in the context of non-invasive glucose monitoring, capable of detecting the glucose concentration in the dermis by just touching the patient's skin with the instrument. Moreover, the LCI system 10 is configured to be readily hand-held to facilitate convenient measurements by a patient without additional assistance in any location.

Figure 4A:
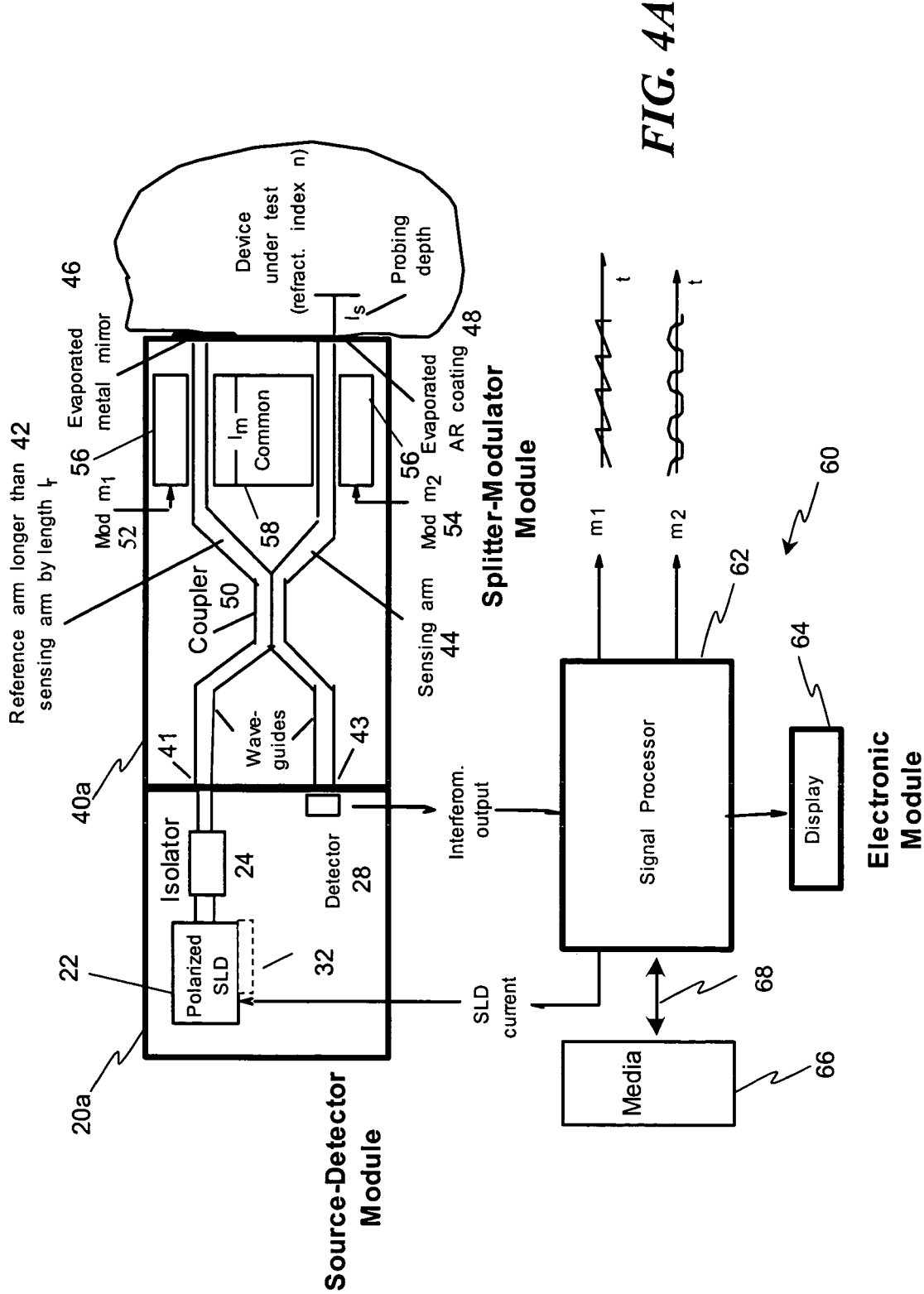
FIG. 4A depicts a minimum configuration interferometer system in accordance with an exemplary embodiment of the invention.

To facilitate appreciation of the various embodiments of the invention reference may be made to FIG. 1, depicting an all-fiber low-coherence interferometer (LCI) system and the mathematical equations developed herein. Referring also to FIG. 4A, in an exemplary embodiment, an LCI system 10 includes, but is not limited to two optical modules: a source-detector module 20a and a splitter-modulator module 40a, and associated processing systems 60. The source-detector module 20a including, but not limited to, a broadband light source 22, such as a super luminescent diode (SLD) denoted hereinafter as source or SLD, attached to a single-mode fiber 23 or waveguide, an isolator 24 configured to ensure that feedback to the broad band light source 22 is maintained at less than a selected threshold. The source-detector module 20a also includes an optical detector 28.

The splitter-modulator module 40a includes, but is not limited to, a waveguide input 41, a waveguide output 43, a splitter/coupler 50, and two waveguide light paths: one light path, which is denoted as the reference arm 42, has adjustable length lr with a reflecting device, hereinafter a mirror 46 at its end; the other light path, which is denoted as the sensing arm 44, allows light to penetrate to a distance z in a medium/object and captures the reflected or scattered light from the medium. It will be appreciated that the captured reflected or scattered light is likely to be only the so-called "ballistic photons", i.e., those that are along the axis of the waveguide. Provision is also made for one or more modulators 52, 54 in each of the reference arm 42 and sensing arm 44 respectively.

Figure 4B:
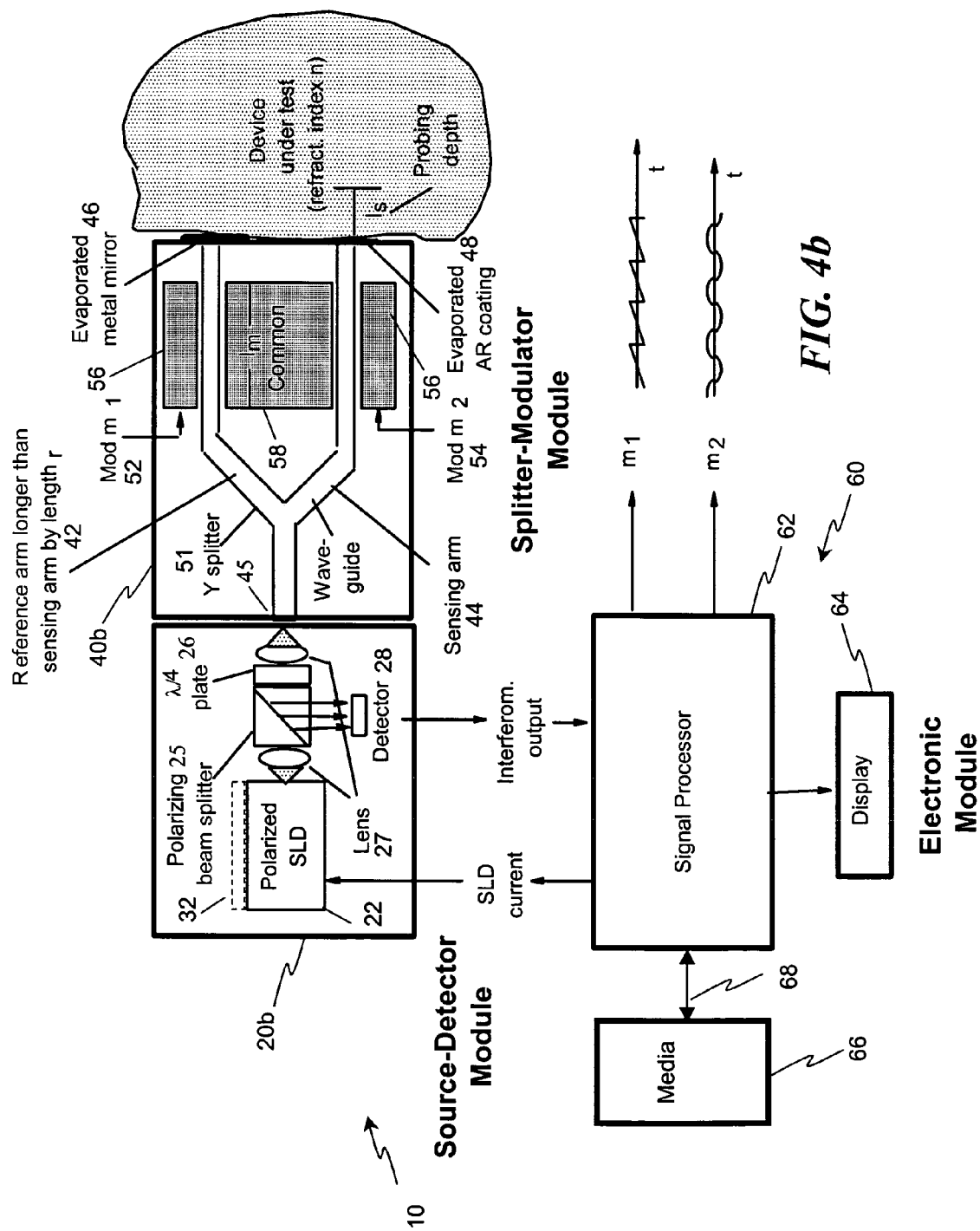
FIG. 4B depicts a configuration of an interferometer system in accordance with an exemplary embodiment of the invention.

Continuing with FIG. 4B as well, in another exemplary embodiment, the source-detector module 20b includes, but is not limited to, a polarized broad-band light source 22, attached to a single-mode fiber 23. The source-detector module 20b also includes a polarizing beam splitter 25 with an quarter wave plate 26 employed to ensure a selected polarization configured to facilitate ensuring that feedback to the broad band light source 22 is maintained at less than a selected threshold. The source-detector module 20b also includes an optical detector 28.

The splitter-modulator module 40b of this embodiment includes, but is not limited to, a waveguide inputs/output 45, a Y-splitter-combiner 51, and the two waveguide arms: reference arm 42, and sensing arm 44. Once again, provision is also made for one or more modulators 52, 54 in each of the reference arm 42 and sensing arm 44 respectively.

It will be appreciated that while certain components have been described as being in selected modules, e.g., 20, 40, such a configuration is merely illustrative. The various components of the LCI system 10 may readily be distributed in one or more various modules e.g., 20, 40 as suits a given implementation or embodiment. Furthermore, in an exemplary embodiment the waveguide arms 42, 44 and/or fibers 23 are configured for single-transverse-mode transmission, and preferably, but not necessarily, polarization-maintaining waveguides or fibers. Furthermore it will be appreciated that in any of the exemplary embodiments disclosed herein the waveguide and/or fiber tips of each component joined are configured e.g., angled-cleaved in a manner to minimize reflection at the junctions.

In order to perform the prescribed functions and desired processing, as well as the computations therefore (e.g., the computations associated with detecting and utilizing the interference signal, and the like), the LCI system 10, and more particularly, the processing system 60, may include, but is not limited to a computer system including central processing unit (CPU) 62, display 64, storage 66 and the like. The computer system may include, but not be limited to, a processor(s), computer(s), controller(s), memory, storage, register(s), timing, interrupt(s), communication interface(s), and input/output signal interfaces, and the like, as well as combinations comprising at least one of the foregoing. For example, computer system may include signal input/output for controlling and receiving signals from the source-detector module 20 as described herein. Additional features of a computer system and certain processes executed therein may be disclosed at various points herein.

The processing performed throughout the LCI system 10 may be distributed in a variety of manners as will also be described at a later point herein. For example, distributing the processing performed in one ore more modules and among other processors employed. In addition, processes and data may be transmitted via a communications interface, media and the like to other processors for remote processing, additional processing, storage, and database generation. Such distribution may eliminate the need for any such component or process as described or vice versa, combining distributed processes in a various computer systems. Each of the elements described herein may have additional functionality that will be described in more detail herein as well as include functionality and processing ancillary to the disclosed embodiments. As used herein, signal connections may physically take any form capable of transferring a signal, including, but not limited to, electrical, optical, or radio.

The light reflected from the reference mirror 46 (Electric field $E_r$) in the reference arm 42 and the light reflected or scattered from depth z within the biological sample (Electric field $E_s$) in the sensing arm 44 are combined at the optical detector 28, whose output current is proportional the combined electric fields. For example, in one instance, the output of the detector is proportional to the squared magnitude of the total electric field $E_t = E_r + E_s$.

The detector current $I_d$ is given by:

$$I_d = \eta |E_r + E_s|^2 = I_r + I_s + 2\sqrt{I_r I_s} G(\tau) \cos 2\pi v_o \tau \quad (1)$$

where $\eta$ is the detector quantum efficiency (typically <1), $I_r = \eta E_r E_r^*$ is the detector current due to $E_r$ alone, $I_s = \eta E_s E_s^*$ is the detector current due to $E_s$ alone, and the * represents the complex conjugate. $E_r E_r^*$ and $E_s E_s^*$ represent the optical power in the reflected reference field and reflected sensing field, respectively. The quantity $\tau$ is the time delay between the reference field $E_r$ and sensing field $E_s$, and is given by:

$$\tau = \frac{l_r}{c} - \frac{z}{c/n} = \frac{l_r - l_s}{c} = \frac{\Delta l}{c} \quad (2)$$

where $I_s = nz$ and $\Delta l = l_r - l_s$ and where $\Delta l$ is the optical path difference between the reference $l_r$ and sensing $l_s$ arms 42, 44, z is the selected or desired target depth in the biological sample, n is the index of refraction in the sample, and c is the speed of light. Also in Equation (1), $v_o$ is the center frequency of the light source 22, and $G(\tau)$ it the cross-correlation function between the reference and sensing fields. Its magnitude is given by:

$$|G(\tau)| = \exp\left[-\left(\frac{\pi \Delta v \tau}{2\sqrt{\ln 2}}\right)^2\right] \quad (3)$$

where $\Delta v$ is the FWHM (full width half maximum) frequency bandwidth of the light source 22.

The last term in Equation (1), the interference term, is the quantity of interest denoted as $i_o$:

$$i_o(\tau) = 2\sqrt{I_r I_s} G(\tau) \cos 2\pi v_o \tau \quad (4)$$

It is convenient to express the interference term $i_o$, in terms of the center wavelength $\lambda_o$ and the path difference $\Delta l$ associated with the interferometer, instead of the frequency and time delay. Therefore, using $v_o \lambda_o = c$, where c is the speed of light in vacuum, $\Delta v$ may be written in terms of the wavelength FWHM bandwidth $\Delta\lambda$, to obtain:

$$i_o(\Delta l) = 2\sqrt{I_r I_s} |G(\Delta l)| \cos \phi_s \text{ where } \phi_s = \frac{2\pi}{\lambda_o} \Delta l \text{ and} \quad (5)$$

$$|G(\Delta l)| = \exp\left[-\left(\frac{\Delta l}{L_c}\right)^2\right] \quad (6)$$

where $L_c$ is the coherence length of the light source and is given by $$L_c = \frac{2\sqrt{\ln 2}}{\pi} \frac{\lambda_o^2}{\Delta\lambda} = 0.44 \frac{\lambda_o^2}{\Delta\lambda}. \quad (7)$$

Figure 2A:
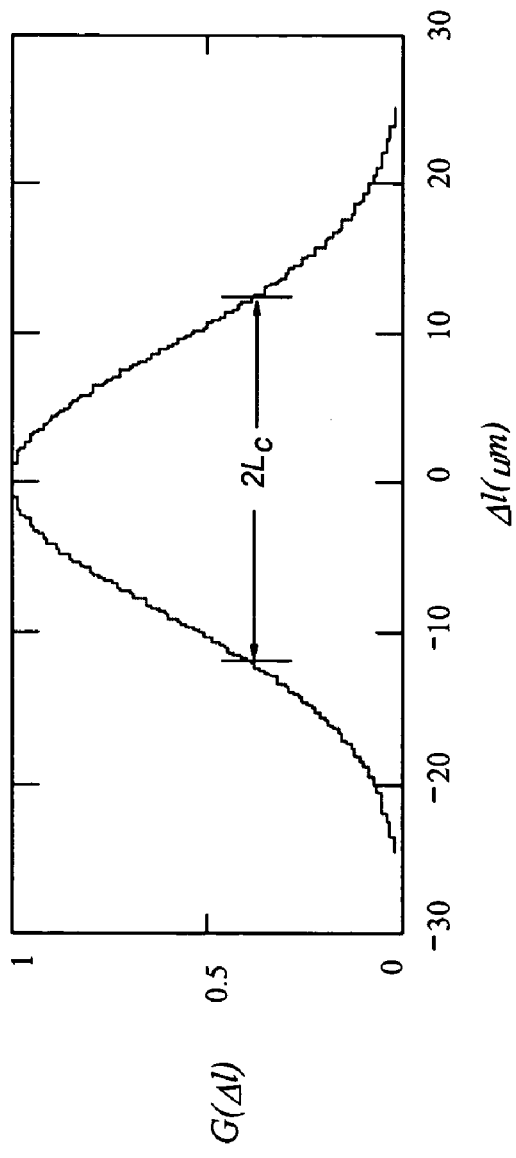
FIG. 2 depicts a plot of the envelope function $G(\Delta l)$ and of the interference signal $G(\Delta l)\cos \phi_s$.
Figure 2B:
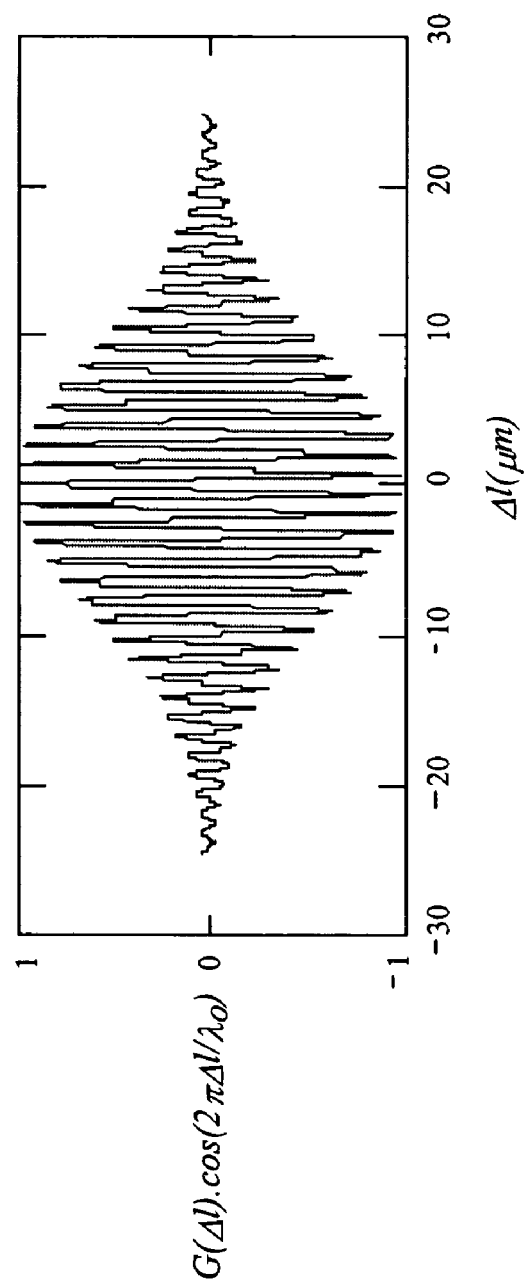

A plot of the envelope function $G(\Delta l)$ and if the interference signal $G(\Delta l) \cos \phi_s$ is shown in FIGS. 2A and 2B respectively, for an interferometer with a light source 22 having center wavelength $\lambda_o = 1.3$ μm and FWHM bandwidth $\Delta\lambda = 60$ nm (coherence length $L_c = 12.4$ μm). The detected interference signal exhibits a maximum when the interferometer is balanced, i.e., when the path difference $\Delta l = 0$. As the system 10 becomes increasingly unbalanced, e.g., $\Delta l \neq 0$, the interference signal exhibits maxima and minima of decreasing amplitude over a range determined by $\Delta l$.

It will be appreciated that the interference signal $i_o$ exhibits significant amplitude only over a spatial window of approximately twice the coherence length $L_c$. As the optical bandwidth increases, the coherence length $L_c$ decreases and the spatial measurement window narrows. Thus, LCI provides a means for probing samples at precisely defined locations within the samples.

It is noteworthy to appreciate that the phase, $\phi_s$, of the interference signal $i_o$ changes by $2\pi$ (from a maximum to a minimum then to another maximum) as $\Delta l$ varies from 0 to $\lambda_o$. Therefore, a small change in $\Delta l$ results in a large phase change. It will be further appreciated that the phase of the interference signal $i_o$ is highly sensitive to small changes of optical properties of the mediums, such as refractive indices, or depth z. Thus, while moderate to large changes may readily be observed by measuring the magnitude of the envelope $G(\Delta l)$, small changes are best detected by measuring the phase $\phi_s$ of the interference signal $i_o$. It will be further appreciated that all the desired information is contained in the range from 0 to $2\pi$. For values of $\Delta l > \lambda_o$, the interference signal $i_o$ is repetitive. Thus, the range from 0 to $2\pi$ as indicated in FIG. 3 is a range for which the desired information can be measured without ambiguity. It may also be noted however, that if the coherence length $L_c$ is short enough that the amplitude difference between the main peak and secondary peaks is measurable, then phase measurement beyond $2\pi$ may be realized.

Therefore, it will be readily be appreciated that there are two types of information, which can be derived from the interference signal $i_o$: the envelope $G(\Delta l)$, or its peak $G(\Delta l=0)$, which may represent scattering, reflection, and absorption; and the more sensitive changes in $\cos \phi_s$ due to small optical property changes in the sample. In order to make any such measurements, it is first preferable to separate the DC components $I_r$ and $I_s$ from $G(\Delta l)$ and $\cos \phi_s$ in the interferometric signal $i_o$ described in Equation (5).

In one or more exemplary embodiments of the invention, several methodologies are disclosed for extracting the pertinent magnitude information from the interference signal $i_o$ described in Equation (5). An exemplary methodology addresses detection of the amplitude/magnitude of the envelope of the interference signal $i_o$.

Continuing now with FIGS. 4A and 4B, the first approach uses a periodic ramp applied to one of the modulators 52, 54. Another approach, also called a homodyne methodology employs a sine wave applied to one of the modulators 52, 54. It will be appreciated that while for the purposes of description of one or more exemplary embodiments, a particular modulator in a particular arm of the LCI system 10 is described as including a modulator, other configurations are conceivable. For example, while the description of an exemplary embodiment calls for modulation of the length of the reference arm of the LCI system 10, manipulation of other optical lengths in the LCI system 10 may be employed for establishing the interference signal and the level of modulation required to achieve the particular desired result.

Using one of the modulators, ($m_1$ 52, for example) or an equivalent means, a ramp modulation is applied to one of the interferometer arms, the reference arm 42, for example, changing $I_r$ over a distance from $-b$ to $a$ over a time period T, such that:

$$\Delta l = \frac{a}{T}t - b \text{ for } t < 0 < T \text{ and if periodic, } \Delta l(t+T) = \Delta l(t). \quad (8)$$

This yields:

$$G(\Delta l)\cos\left(\frac{2\pi}{\lambda_o}\Delta l\right) = \exp\left[-\left(\frac{\frac{a}{T}t-b}{L_c}\right)^2\right]\cos\left[\frac{2\pi}{\lambda_o}\left(\frac{a}{T}t-b\right)\right] \text{ and,} \quad (9)$$

$$i_o(t) = 2\sqrt{I_r I_s}\cos(2\pi f_c t - \phi_c) \text{ where } f_c = \frac{a}{\lambda_o T} \text{ and } \phi_c = \frac{2\pi b}{\lambda_o}. \quad (10)$$

Figure 5:
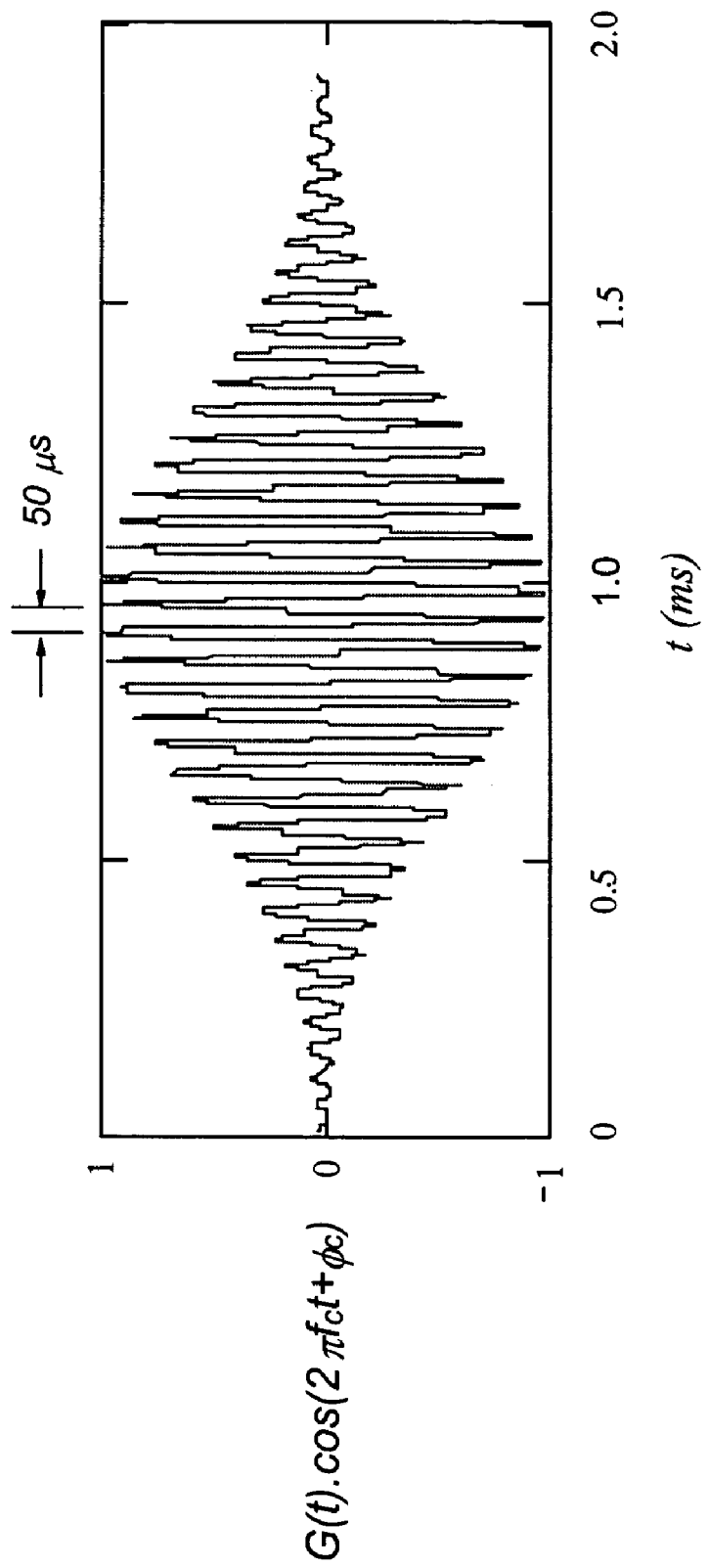
FIG. 5 depicts a plot of the interference signal for a single ramp.

The resultant of the modulation represents a sine wave of frequency $f_c$ with an arbitrary phase $\phi_c$ determined by b, which is amplitude-modulated (AM) by the $G(\Delta l)$ envelope function, now also a function of time. FIG. 5 depicts a plot of the function in equation (9) for a single ramp sweeping over $\pm 2L_c$ for the light source example used earlier, with $a=4L_c$ and $b=2Lc$), and for T=1.9 ms, we get $f_c$=20 KHz. When the ramp function used for modulation is periodic, this signal repeats with the periodicity of the ramp function. Advantageously, the interference signal may be readily envelope-detected in similar fashion to an AM receiver signal, to obtain $G(\Delta l)$, and peak-detected, preferably in an iterative fashion, to yield $G(\Delta l=0)$, which can then be digitized for further processing.

Figures 6, 7:
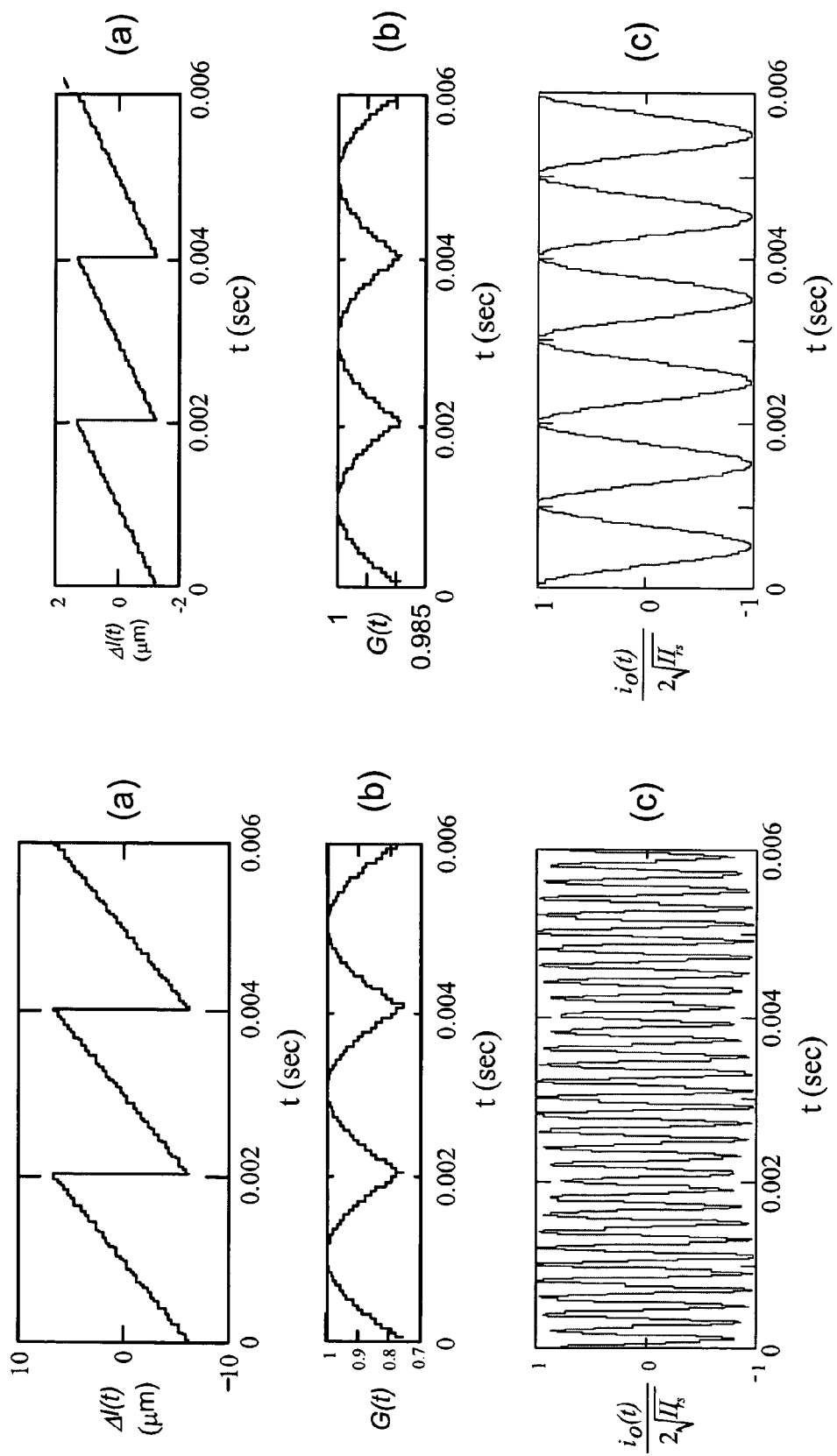
FIG. 6A depicts the values of $\Delta l$ for a periodic ramp for $a=5\lambda_o$ and $b=0.5a$.
FIG. 6B depicts the envelope function as a function of time for the particular G(t) for $a=5\lambda_o$ and $b=0.5a$.
FIG. 6C depicts the output current or interference signal for $a=5\lambda_o$ and $b=0.5a$.
FIG. 7A depict the values of $\Delta l$ for a periodic ramp for $a=\lambda$ and $b=0.5a$.
FIG. 7B depicts the envelope function as a function of time for the particular G(t) for $a=\lambda_o$ and $b=0.5a$.
FIG. 7C depicts the output current or interference signal for $a=\lambda_o$ and $b=0.5a$.

It should be noted that it is not essential to scan over as wide a range (e.g., $\pm 2L_c$) in order to obtain the peak of the envelope, e.g., $G(\Delta l=0)$. Advantageously, it is sufficient to ramp over as little as just one wavelength, using $a=\lambda_o$ and $b=\lambda_o/2$. The resultant signal is almost a pure sine wave or one that is slightly amplitude-modulated by $G(\Delta l)$. FIGS. 6 and 7 illustrate the response to a periodic ramp for modulator sweeps with $a=5\lambda_o$ and for $a=\lambda_o$ respectively, and $b=a/2$. FIGS. 6A and 7A depict the values of $\Delta l$, while FIGS. 6B and 7B depict the envelope function as a function of time for the particular G(t) $\Delta l$ respectively, and FIGS. 6C and 7C depict the output current or interference signals for each $\Delta l$, respectively.

Observation of the figures makes it evident that for $a=\lambda_o$ there is little need for filtering before peak detection to obtain the amplitude as the ripples in the envelope from peak to peak are quite small. For larger values of a, as depicted for FIGS. 6A-6C, a simple filtering technique with a center frequency around $f_c$ is sufficient to separate the modulation $G(\Delta l)$ [or now G(t)] from the carrier at $f_c$ if desired.

In an exemplary embodiment, once the magnitude of the interferometric signal $i_o$ is ascertained, for a selected target depth z, additional LCI signal magnitudes corresponding to other target depths are acquired. Furthermore, if desired, in order to obtain averaged distributions of the LCI signal intensity vs. depth multiple scans corresponding to multiple target depths may be employed. As disclosed herein, there are several methodologies and exemplary LCI systems that may be employed to acquire an interferometric signal $i_o$ corresponding to selected depths. In one exemplary embodiment, the modulator $m_1$ 52 may be employed to add an additional offsets denoted as $\Delta$ to the reference arm 42 corresponding to a group of target depth variations $\Delta z$ in the vicinity of target depth z. This approach is readily implemented employing the LCI system 10 of FIGS. 4A and 4B. It will be appreciated that the extent of such variations in the target depth $\Delta z$ are a function of the geometry of the waveguide arm and modulators employed. Additional details regarding the waveguide arms 42, and 44 and the configuration of the modulators $m_1$ 52 an $m_2$ 54 are addressed at a later point herein. In addition, an extension module (described at a later point herein) may also be implemented to facilitate variations in target depth and depth scans.

To address an example wherein an exemplary embodiment of the invention may be employed for detection and monitoring of glucose concentration, it is well known that the presence of glucose affects the light scattering properties of tissue. An increase of glucose concentration decreases the scattering coefficient of tissue $\mu_s$. The value of $\mu_s$ depends on the mismatch of the refractive index n of the Interstitial Fluid (ISF) and the refractive index of the scattering centers in the tissue-cell membranes, cellular components and protein aggregates. As stated earlier, raising the glucose concentration in the ISF raises the ISF refractive index by approximately $1.52 \times 10^{-6}$ per each mg/dl and thus decreases the refractive index mismatch, leading to a decrease of the scattering coefficient $\mu_s$.

Turning now to ascertaining a glucose concentration employing magnitudes for an exemplary embodiment, based on a depth profile or depth variations in the vicinity of a target depth z. Based on a single-scattering regime, the Beer-Lambert law may be used to model the attenuation of the light flux through the skin as $I(z)=I_0 \exp(-\mu_t z)$, where z is the target depth, and $\mu_t=\mu_a+\mu_s$ is the total attenuation coefficient, $\mu_a$ is the absorption coefficient, and $\mu_s$ is the scattering coefficient. Advantageously, for light at 1,300 nm for illustration, $\mu_a$ is negligible, and the total attenuation coefficient $\mu_t$ may readily be approximated as $\mu_t \approx \mu_s$. Therefore it may be seen that the slope of the profile of I(z) may be used to approximate the values of the scattering coefficient $\mu_s$ and therefrom, the glucose concentration. The scattering coefficient is obtained by plotting the LCI amplitude profile on a logarithmic scale and measuring the slope of the logarithmic profile. Changes in the slope of the measured magnitudes/intensities may be recorded in order to monitor scattering coefficient changes, which are related to the index of refraction in the sample and thereby, variations ISF glucose levels. Thus, a glucose concentration may be determined employing as few as two magnitudes corresponding to two target depths or a target depth and a variation in its vicinity. In an exemplary embodiment, a comparison of current measurements for scattering coefficient and/or index of refraction and a baseline measurement based on calibration and/or normalization for a particular patient yields an accurate means of determining the current glucose concentration.

Correlations of glucose concentrations between LCI-based non-invasive measurements employing such methodologies and invasive measurements in the range of about 80-95% can be achieved. It will further be appreciated that when compared to other analytes, glucose, sodium chloride (NaCl), potassium chloride (KCl), and urea produced the highest changes in ISF refractive index, and consequently in scattering coefficient $\mu_s$ with glucose exhibiting the most pronounced effect.

Figure 8:
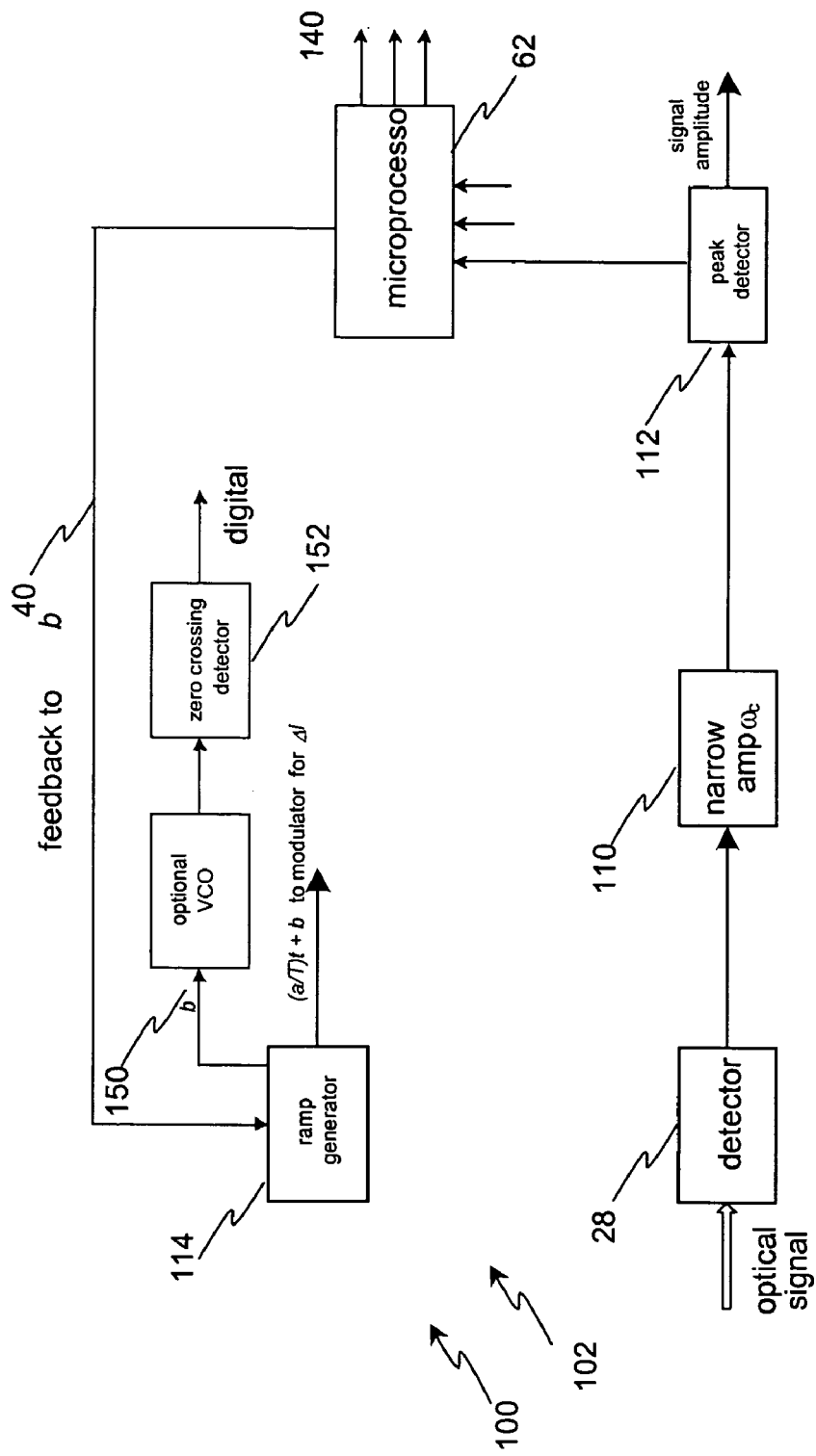
FIG. 8 depicts an a simplified block depicting a detection scheme employing ramp modulation.

FIG. 8 depicts a illustrative implementation of the processes 100 that may be employed in accordance with an exemplary embodiment of the invention for determination of the magnitude of the interference signal $i_o$. The bolded portions of FIG. 8 depict an implementation, which may be employed for a detection scheme using the ramp modulator for magnitude determination. The optical signal is observed at the optical detector 28 and applied to a narrowband amplifier/filter 110 resulting in the interference signal $i_o$. The interference signal is applied to a peak detector 112 to facilitate determination of the magnitude of the envelope of the interference signal $i_o$. A ramp generator 114 is utilized as the input to modulator $m_1$ 52 (FIGS. 4A and 4B) to facilitate manipulation of the length of one of the arms, in this instance, the reference arm 42 of the LCI system 10.

It is well known that the refractive index change $\Delta n$ in the dermis due to the presence of glucose is ~$1.52 \times 10^{-6}$ per milligram per deciliter (mg/dl). Assuming a linear dependence, this gives a glucose concentration C of $$C = 6.58 \times 10^5 \Delta n \text{ mg/dl} \tag{11}$$

With the numbers given above, it will be appreciated that glucose levels from about 0.0026 mg/dl to about 855 mg/dl can be measured at 1-mm probing depth. Similarly, glucose levels from about 0.0013 mg/dl to about 428 mg/dl at 2-mm probing depth. The acceptable glucose concentration in humans ranges from about 70 mg/dl to about 170 mg/dl. Therefore, it is evident that the methodologies disclosed provide a significant benefit when applied particularly to glucose monitoring.

Referring once again to FIGS. 4A and 4B, broadband light sources including, but not limited to, SLD's are laser type structures configured and designed to operate substantially without feedback, e.g., of the order of less than $10^{-3}$, preferably less than $10^{-4}$, more preferably less than $10^{-5}$. In the presence of feedback, the spectrum of the SLD light source 22 may be distorted, the coherence is significantly increased and the spectrum can exhibit very large ripples and even lasing spikes, and thereby may become lasers. Therefore, to prevent distortion and maintain spectral integrity, low coherence, and broadband characteristics, reflections back into the light source 22 are avoided to maintain a broadband light source 22. Thus, in an exemplary embodiment of the LCI system, isolation is provided to alleviate feedback to the light source 22.

Continuing with FIGS. 4A and 4B, in an exemplary embodiment, the source-detector module 20a, 20b, is configured to prevent the reflected interferometer light from reaching the SLD light source 22 and upsetting its operation. The SLD source 22 is designed and configured such that it is linearly-polarized. SLDs and lasers are "heterostructures" semiconductor devices consisting of a thin "active" layer sandwiched between two "cladding" layers of lower refractive index, all epitaxially grown on a single crystal substrate 23. One such process for fabrication is known as MOCVD (metalorganic chemical vapor deposition). One of the cladding layers is p-doped, and the other is n-doped. The substrate 23 is typically n-doped, and the n-cladding layer is the first to be deposited on it. The structure forms a p-n semiconductor junction diode, in which the active layer is caused to emit light of energy equal to its bandgap upon the application of an electric current.

The structure is called heterostructure because the active and clad layers are made of different material. This is in contrast with ordinary diodes in which the p-n junction is formulated between similar materials of opposite doping. The use of heterostructure has made it possible to confine the electrical carriers to within the active region, thus providing high efficiency and enabling operation at room temperature. In many heterostructures, light is emitted in both TE polarization (the electric field in the plane of the layer) and TM polarization (electric field perpendicular to the layer).

However, useful effects are obtained when the active layer is sufficiently thin such that quantum mechanical effects become manifest. Such thin layers are called "quantum well" (QW) layers. Furthermore, the active layer can be "strained", i.e., a slight mismatch (of about 1%) with respect to the substrate crystal lattice can be introduced during the deposition of the QW layer. The strain can modify the transition characteristics responsible for light emission in beneficial ways. In particular, the light is completely polarized in the TE mode if the strain is compressive. Thus, it is now possible to make a linear polarized laser or broadband SLD by compressive strain of the active layer. In an exemplary embodiment, such a linearly-polarized light source 22 is employed.

In one exemplary embodiment, as depicted in FIG. 4A, the light from the light source 22 is directed through an isolator 24 configured to transmit light in one direction, while blocking light in the opposite direction. The light is directed to a splitter/coupler 50 of the splitter-modulator module 40a. The source-detector module 20a also contains a detector 28 to receive from the splitter/coupler 50.

In another exemplary embodiment as depicted in FIG. 4B, the linearly-polarized light from the SLD light source 22 is collimated with lenses 27 and applied to a splitter 25. If a basic 50/50 splitter 24 is employed, half of the returned light goes to the detector 28 and the other half is directed to the SLD light source 22. Once again, in this configuration an isolator 24 may be employed to prevent feedback to the light source 22. Similarly, as stated earlier, in another exemplary embodiment, the splitter 25 is a polarizing beam splitter 25 operating in cooperation with a quarter wave plate 26, employed to prevent feedback light from reaching the light source 22. The polarizing beam splitter 25 facilitates the elimination of feedback to the SLD light source 22 by redirecting substantially all the reflected light from the splitter-modulator module 40b to the detector 28.

The splitter 25 transmits the horizontally polarized light to the quarter wave plate 26, which coverts the light to another polarization, (for example, circular polarization). Likewise, the returning, circularly polarized light is received by the quarter wave plate 26 and is reconverted to a linear polarization. However, the linear polarization opposite, for example, vertical. The vertically polarized light is transmitted to the polarizing beam splitter 25, which directs all of the light to the detector 28. Advantageously, this approach transmits substantially all of the light i.e., the interference signal, to the detector 28. Whereas embodiments employing the isolator 24 transmits approximately half of the light to the detector 28.

The polarizing beam splitter 25 is a device that transmits light of one polarization (say the horizontal, or TE-polarized SLD light) and reflects at 90° any light of the other polarization (e.g., vertical or TM-polarized). The quarter-wave plate 26 is a device that converts a linearly polarized incident light to circular polarization and converts the reflected circularly-polarized light to a linearly-polarized of the other polarization which is then reflected at a 90° angle by the polarizing beam splitter 25 to the detector 28. Therefore, essentially all the light transmitted by the light source 22 is re-polarized and transmitted to the splitter-modulator module 40b and all the reflected light from the sample and reflecting device 48 is deflected by the polarizing beam splitter 25 to the detector 28. Advantageously, this doubles the light received at the detector 28 relative to the other embodiments, and at the same time minimizes feedback to the SLD light source 22.

In an exemplary embodiment an SLD chip for the light source 22 has dimensions of approximately 1 mm×0.5 mm×0.1 mm (length×width×thickness), and emits a broadband light typically of up to 50 mW upon the application of an electric current of the order of 200-300 mA. The light is TE-polarized if the active layer is a compressively strained QW. The FWHM spectrum is of the order of 2% to 3% of the central wavelength emission. A SLD light source 22 with 1.3 μm center wavelength emission and operating at 10 mW output power at room temperature would have a bandwidth of about 40 nm and would require about 200 mA of current. In an exemplary embodiment, for continuous wave (cw) operation at room temperature, the SLD light source 22 may be mounted on an optional thermoelectric cooler (TEC) 32 a few millimeters larger than the SLD light source 22 chip to maintain the temperature of the light source 22 within its specified limits. It will be appreciated that the SLD light source 22 and associated TEC 32 peripherals in continuous operation would have the largest power consumption in the LCI system 10. However, without the TEC 32, the SLD junction temperature would rise by several degrees under the applied current and would operate at reduced efficiency.

Advantageously, in yet another exemplary embodiment, the utilization of a TEC 70 may readily be avoided without incurring the effects of significant temperature rise by pulsed operation of the SLD light source 22. Pulsed operation has the further advantage of reducing the SLD electrical power requirement by a factor equal to the pulsing duty cycle. Moreover, for selected applications of digital technology and storage, only a single pulse is sufficient to generate an interference signal and retrieve the desired information. Therefore, for example, with pulses of duration 10 μs and 1% duty factor, the LCI system 10 of an exemplary embodiment can average 1000 measurements per second without causing the SLD light source 22 temperature to rise significantly. Thus, for low power consumption, the LCI system 10 should preferably be designed for the SLD light source 22 to operate in a pulsed mode with a low duty cycle and without a TEC 32. In such a configuration the source-detector module 20 would be on the order of about 2 centimeters (cm)×2 cm×1 cm.

The splitter-modulator module 40a, and 40b of an exemplary embodiment includes a splitter/coupler 50 and Y-splitter/combiner 51 respectively, with a "reference" arm 42 and a "sensing" arm 44, the reference arm 42 having a slightly longer optical path (for example, 1 to 3 mm for measurements in biological tissues) than the sensing arm 44. The optical path difference between the two arms 42, 44 is configured such that the LCI system 10 balanced for the chosen probing depth z. Provision is also made to include a modulator $m_1$ 52 and $m_2$ 54 in the reference arm 42 and sensing arm 44 respectively.

In an exemplary embodiment, the splitter/coupler 50, Y-splitter/combiner 51 reference arm 42 and a sensing arm 44 are formed as waveguides in a substrate. However, other configurations are possible, including but not limited to separate components, waveguides, optical fiber, and the like. The substrate 23 for this module should preferably, but not necessarily, be selected such that the waveguides of the arms 42, 44 and modulators 52, 54 can be fabricated on/in it by standard lithographic and evaporation techniques. In one exemplary embodiment, the waveguides of the arms 42, 44 are fabricated by thermal diffusion of titanium or other suitable metal that increases the index of refraction of the substrate, evaporated through masks of appropriate width for single transverse-mode operation. In another exemplary embodiment, the waveguides are formed by annealed proton exchange in an acid bath. This process raises the refractive index in the diffusion region, thus creating a waveguide by virtue of the refractive index contrast between the diffusion region and the surrounding regions. In an exemplary embodiment, is lithium niobate (LiNbO3) is employed as a substrate 23. It will be appreciated that other possible materials, namely ferroelectric crystals, may be utilized such as lithium tantalite (LiTaO3) and possibly indium phosphide depending on configuration and implementation of the LCI system 10.

Lithium niobate is a ferroelectric crystal material with excellent optical transmission characteristics over a broad wavelength range from the visible to the infrared. It also has a high electro-optic coefficient, i.e., it exhibits a change of refractive index under the application of an external electric field. The refractive index change is proportional to the electric field. The speed of light in a transparent solid is slower than in vacuum because of its refractive index. When light propagates in a waveguide built into the electro-optic material, an applied electric field can alter the delay in the material, and if the electric field is time-varying, this will result in a phase modulation of the light. The LiNbO3 material is very stable, the technology for making it is mature, and LiNbO3 modulators, which can be compact and are commercially available.

In an exemplary embodiment, the high electro-optic coefficient (refractive index change with applied electric field) of lithium niobate is exploited to facilitate implementation of a modulator, such as modulators $m_1$ 52 and $m_2$ 54. In this embodiment, a modulator is implemented on or about the waveguide arms 42, 44, by depositing metal electrodes 56, 58 in close proximity to the waveguide arms. In one embodiment, the metal electrodes 56, 58 are deposited on the sides of the waveguide arms 42, 44. In another, the metal electrodes 56, 58 may be deposited on the waveguide arms 42, 44 with an appropriate insulation layer, in a selected region. FIGS. 4A and 4B also shows a diagrammatic depiction of a modulators $m_1$ 52, $m_2$ 54 in each arm 42, 44 fabricated by depositing metal films (electrodes) 56 on the outside the waveguides and a larger "common" electrode 58 between them. Modulation with modulator $m_1$ 52 is obtained by applying a voltage between the upper electrode 56 and the common electrode 58, and modulation with modulator $m_2$ 54 is obtained by applying a voltage between the lower 56 and the common electrodes 58. The change of refractive index with applied voltage results in a delay or a change of optical path between for the modulated arm 52, 54. For a given applied voltage, the optical path change depends on the length of the electrodes 56, 58.

Figure 9:
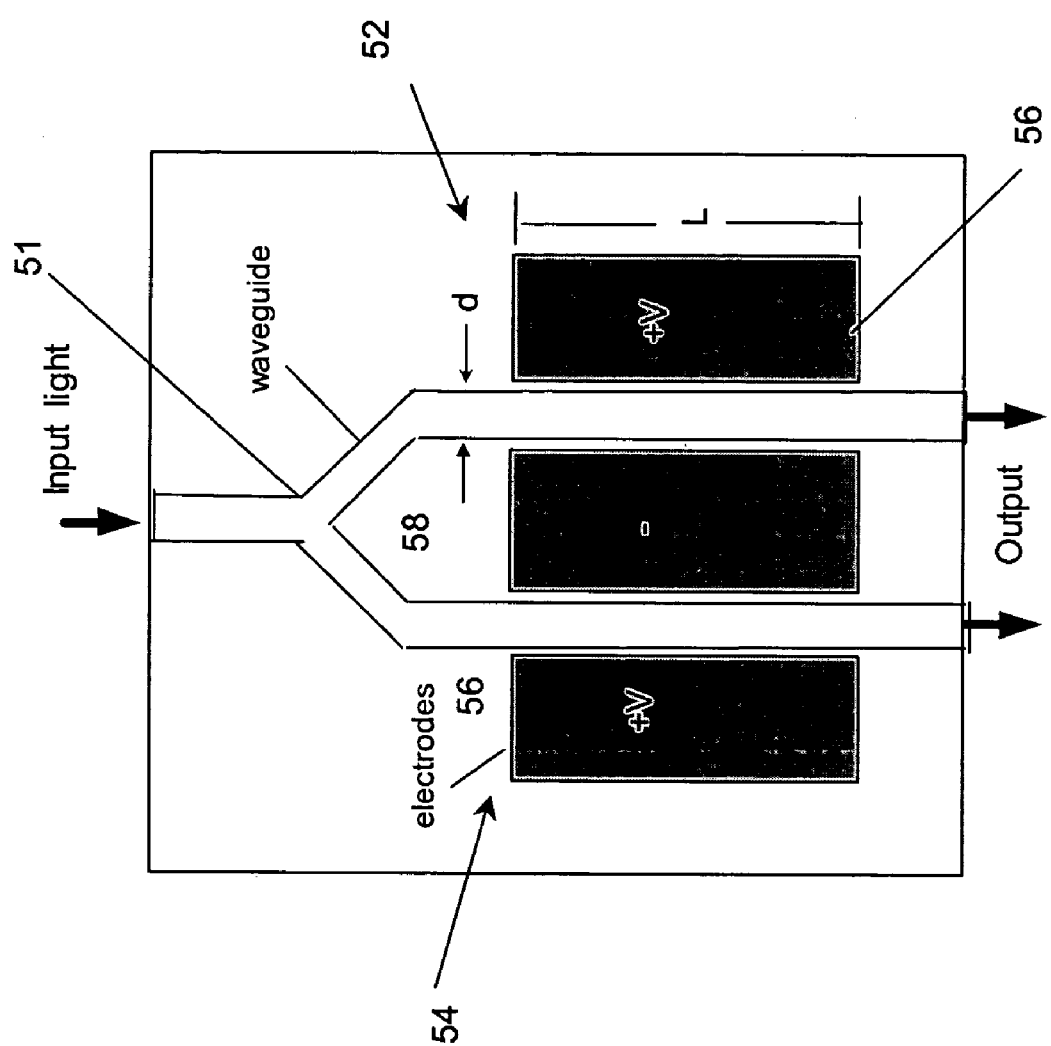
FIG. 9 depicts an illustration of a splitter-modulator module in accordance with an exemplary embodiment.

FIG. 9 depicts an illustration of a splitter-modulator module 40b with a Y-splitter 51 and two modulators 52, 54 integrated on a LiNbO3 substrate 23. One method of making the Y-splitter 51 (or splitter/combiner 50 of splitter-modulator module 40a) and waveguide arms 42, 44 is by diffusing titanium or another suitable metal into a substrate 23 at high temperature. Another method of fabrication is by proton exchange in an acid bath. In an exemplary embodiment, titanium and a lithium niobate substrate 23 are employed. The process of fabricating the module 40b (or 40a) is illustrated in FIGS. 10A-C. In the diffusion process, the waveguide pattern is etched in a mask and a thin layer of titanium is vacuum-deposited onto the substrate 23 through the mask. The substrate 23 is then heated in an oven at about 900-1000 degrees C. to diffuse the titanium into the lithium niobate substrate 23. The index of refraction of the diffusion region is slightly higher than that of the surrounding material, and this constitutes waveguides in which light is guided in the diffusion region by virtue of its higher refractive index (just as in an optical fiber where the light propagates in the higher index core). Following diffusion, the metal electrodes 56 and 58 for the modulator(s) 52, 54 are deposited on the sides as shown, with a small spacing d between them. Application of a voltage V between one of the outer electrodes 56 and the negative center electrode 58 establishes an electric field of value V/d across the waveguide e.g. reference arm 42 and/or sensing arm 44. In an exemplary embodiment, the width of the waveguide is approximately 3-5 microns, and the spacing d is only a few more microns wider.

The refractive index change due to the electro-optic effect is given by $$\Delta n = -\frac{1}{2} n_o^3 r \frac{V}{d} \quad (12)$$

where $n_o$ is the refractive index, and r is the electro-optic coefficient. The phase shift of a light of wavelength $\lambda$ propagating in a LiNbO3 modulator is given by $$\Delta \phi = \pi \frac{L}{\lambda} n_o^3 r \frac{V}{d} \quad (13)$$

where L is the length of the modulator electrodes 56, 58. In the context of the LCI systems 10 disclosed herein, this corresponds to an optical path length change of $$\Delta l = \frac{1}{2} n_o^3 r L \frac{V}{d} \quad (14)$$

Typical material properties are:

$r$=11.3×10-12 m/V $n_o$=2.35

To obtain larger scale modulations, it will be appreciated that an increase in the voltage on/or the length of the modulator will result in larger changes in the index of refraction by the modulator, resulting in an increased variation of the corresponding phase delay. For example, with a configuration of d=10 microns, an applied voltage of only 3.6 volts is sufficient to yield a value of Δl or b (as discussed above) of 1.3 microns (the wavelength of the light discussed in the examples above). This illustrates that a modulator with a range equivalent to the wavelength λ (for example) 1.3 microns may readily be achieved employing the configuration described.

In an exemplary embodiment, the reference arm 42 is terminated in an evaporated mirror (metal or quarter-wave stack) 46, and the sensing arm 44 is terminated in an anti-reflection (AR) coating, or is covered with an index-matching agent 48 that prevents or minimizes reflection from the end of the sensing arm 44 when placed in contact with the object to be measured. In such a configuration splitter-modulator module 40 would be on the order of about 2 cm×2 cm×0.5 cm.

Figure 11:
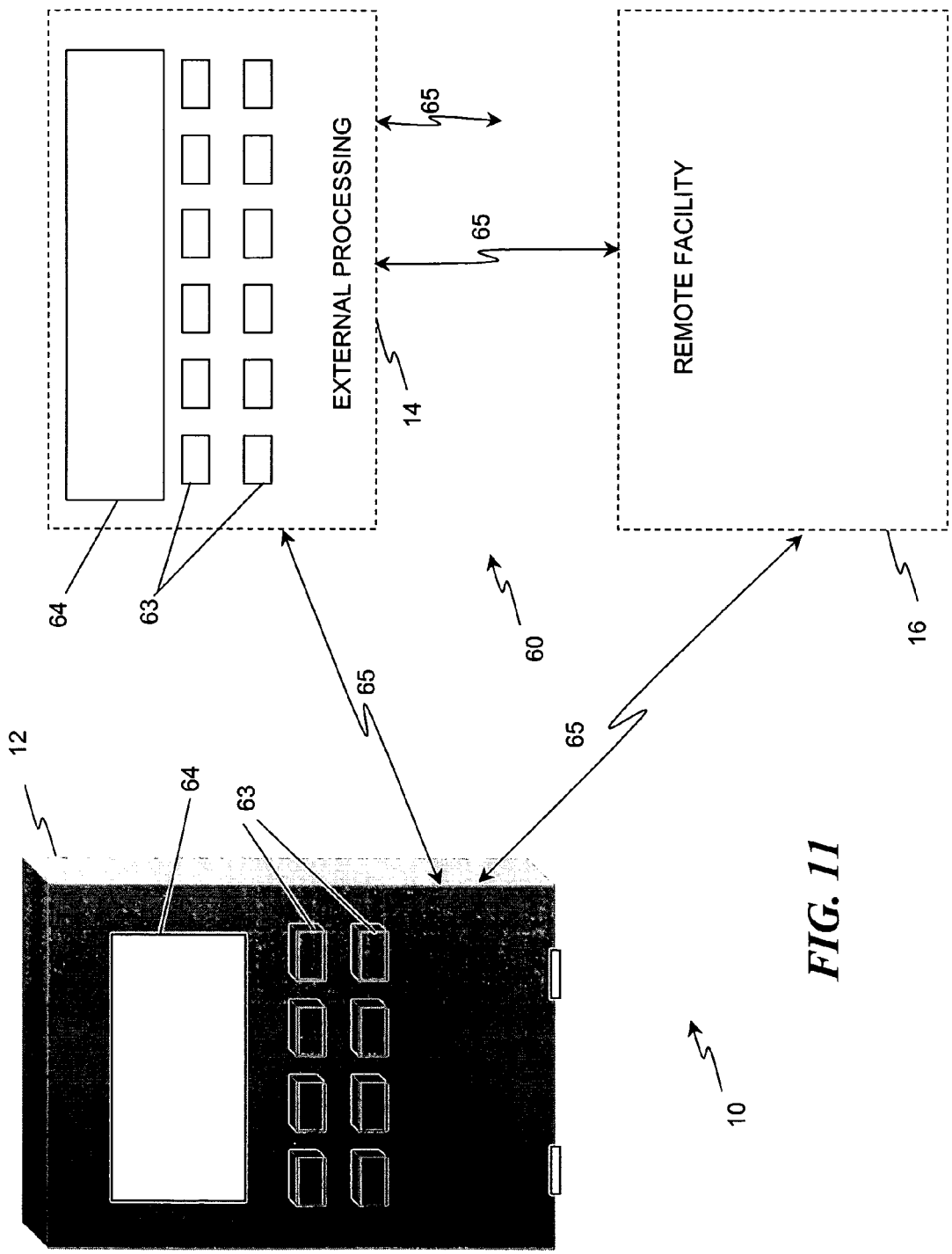
FIG. 11 depicts a miniaturized, handheld LCI system in accordance with an exemplary embodiment.

Referring now to FIG. 11, a miniaturized, optionally handheld, LCI system 10 is depicted in accordance with an exemplary embodiment. In an exemplary embodiment, the LCI system 10 is packaged in a small enclosure 12 and includes, but is not limited to, various modules including, but not limited to source-detector module 20a, 20b, splitter-modulator module 40a, 40b and may include one or more additional extension, adapter or interface modules such as 80, 90, and 92 (See FIGS. 4A, 4B and 13-16) or even calibration strip 70. In addition, also optionally packaged within the enclosure may be processing system 60, including processor 62 (not shown in this view) associated controls 63 e.g., keys, selectors, pointers, and the like, display 64, data media 66, as well as communication interfaces 65, and the like as well as rechargeable batteries. Therefore, in one exemplary embodiment the LCI system 10 as packaged in enclosure 12 should be comparable in size to that of a typical cell phone or a Personal Digital Assistant (PDA), i.e., about 4 cm×6 cm×1 cm. to readily facilitate handheld operation.

Continuing with FIG. 11, it should also be appreciated as mentioned earlier, that various portions of the LCI system 10, and particularly, processing system 60 may be enclosed within the enclosure 12, or associated with an external processing unit 14, or remotely located, such as with a computer processing system 60 in another facility 16. In yet another exemplary embodiment, the LCI system 10 may also include communication interfaces 65, including wireless interfaces (e.g., infrared, radio frequency, or microwave transmitter/receiver) similar to modern computers, cell phones, PDAs, and the like to enable communication, including, but not limited to Internet communication, with external systems 14 and remote facilities 16. For example, as a non-invasive glucose monitor and controller, a sensing portion including the source-detector module 20a, 20b and splitter-modulator module 40a, 40b can be detachable, in the form of a wrist band or wrist watch for continuous monitoring, while the rest of the remainder of the LCI system 10 may be in a patient's pocket, separate computer, at a doctor's office, and the like.

Figure 12A:
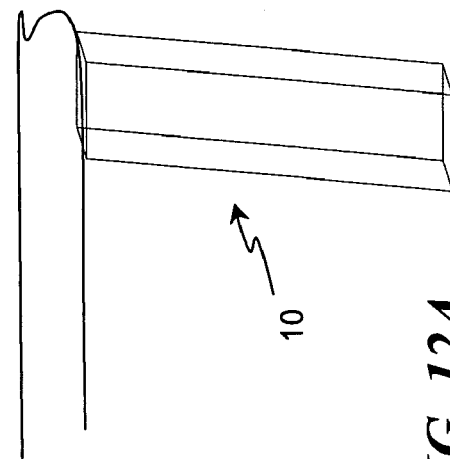
FIG. 12A depicts operation of a miniaturized, handheld LCI system in accordance with an exemplary embodiment.
Figure 12B:
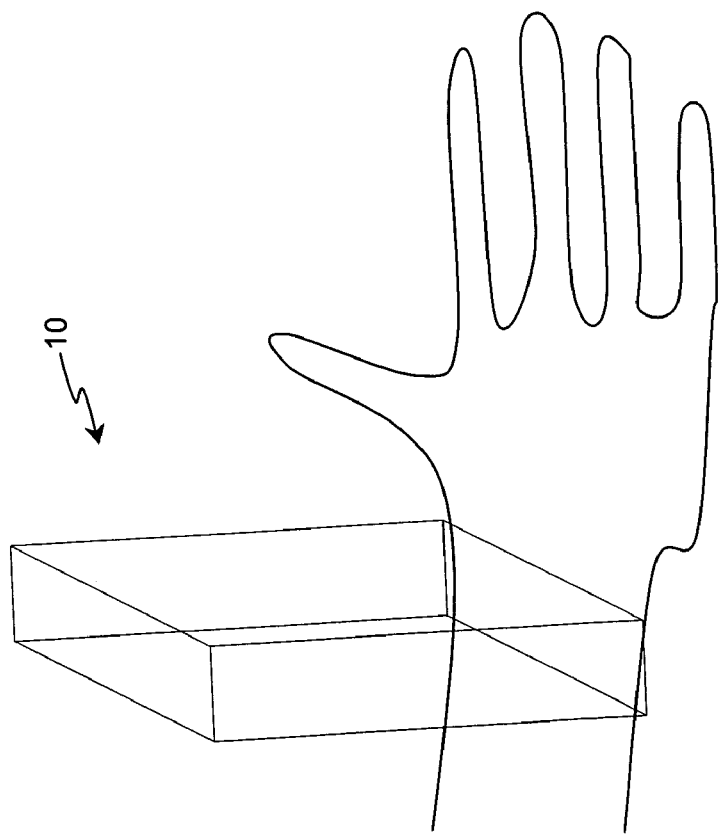
FIG. 12B depicts operation of a miniaturized, handheld LCI system in accordance with another exemplary embodiment.

Referring now to FIGS. 12A and B, to illustrate operation of the LCI system 10, as a non-invasive glucose monitor, the instrument is placed against the skin at some location such as the finger, the back of the hand, or the arm. It should be noted that the finger presents a desirable location for sensing, since it has no hair and few other features that may interfere with the light path. However, other locations are possible. The LCI system 10 would rapidly measure and determine the glucose concentration, (or a multitude of measurements can be made and averaged over a few seconds). A display 66 may also be utilized to provide visual information with respect to measurement to a patient. Furthermore, the LCI system 10 could be coupled to a dispenser embedded in the patient for real-time control and administration of medications such as, insulin.

Figure 13:
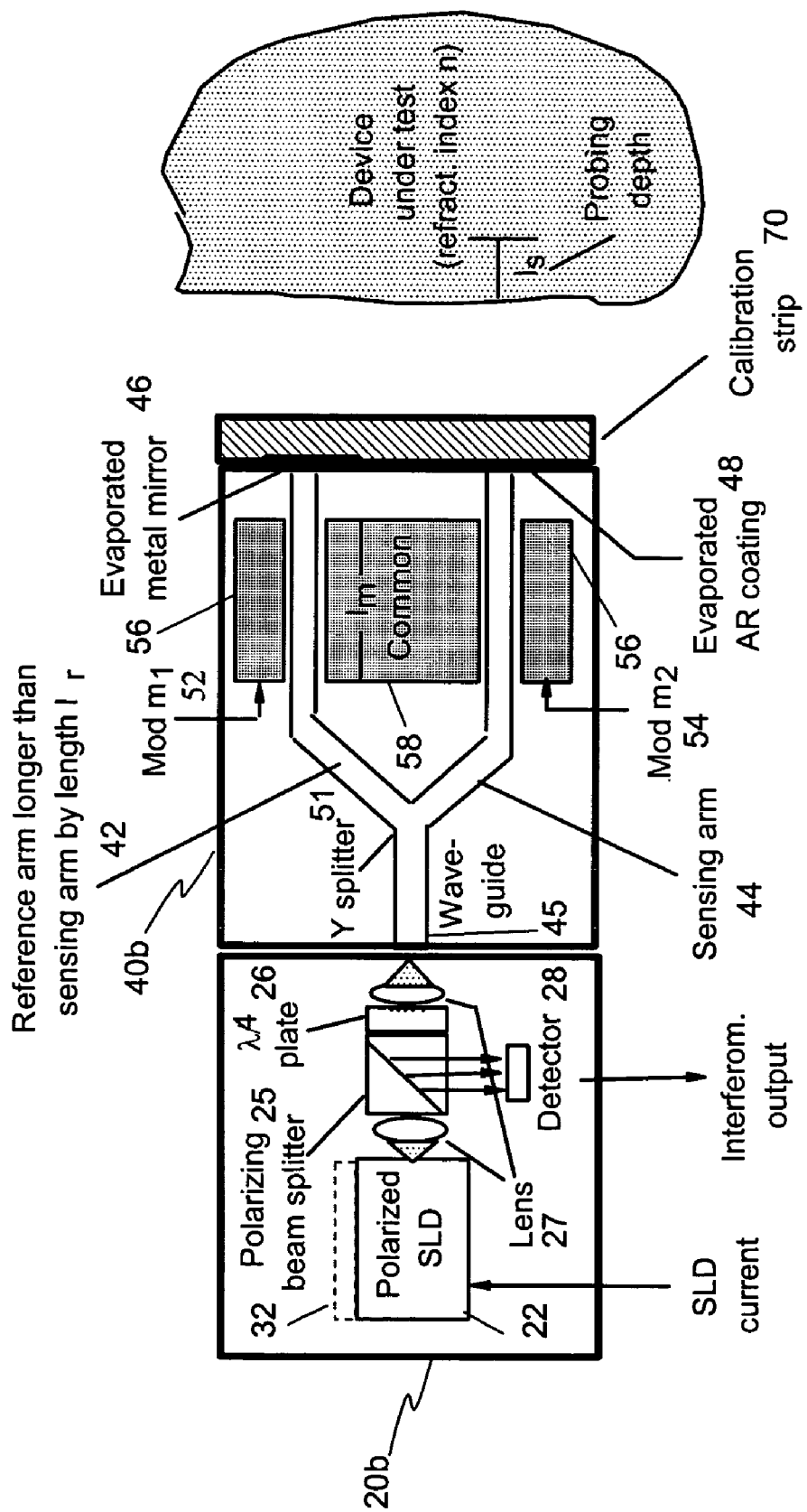
FIG. 13 depicts an adaptation of the interferometer system of FIGS. 4A and 4B with a calibration strip.

The phase associated with a selected length of the reference arm is pre-calibrated to correspond to a set distance (about 1 to 3 mm) under the skin. The spot size for the light at the tip of the sensing fiber or waveguide of the sensing arm 44 is on the order of a few microns. The LCI system 10 may readily be calibrated by placing a strip of known refractive index (or, in the case of a glucose monitor, known glucose content,) and appropriate thickness at the sensing end of the splitter-modulator module 40 prior to performing a measurement. FIG. 13 depicts the LCI system of FIGS. 4A and 4B with a calibration strip in place. The calibration strip 70 can serve the dual purpose of calibration and refractive index matching. Its placement in contact with the splitter-modulator module 40a, 40b does not affect the reference arm 42, since the reference arm light does not penetrate it due to the presence of the end mirror 46. The calibration strip 70 and associated processing may be configured such that the LCI system 10 provides a first reading when the calibration strip 70 is not in contact with the LCI system 10 and a corrected reading when in contact with the calibration strip. Furthermore, the calibration strip may be configured as a disposable item.

Figures 14A, 14B, 14C:
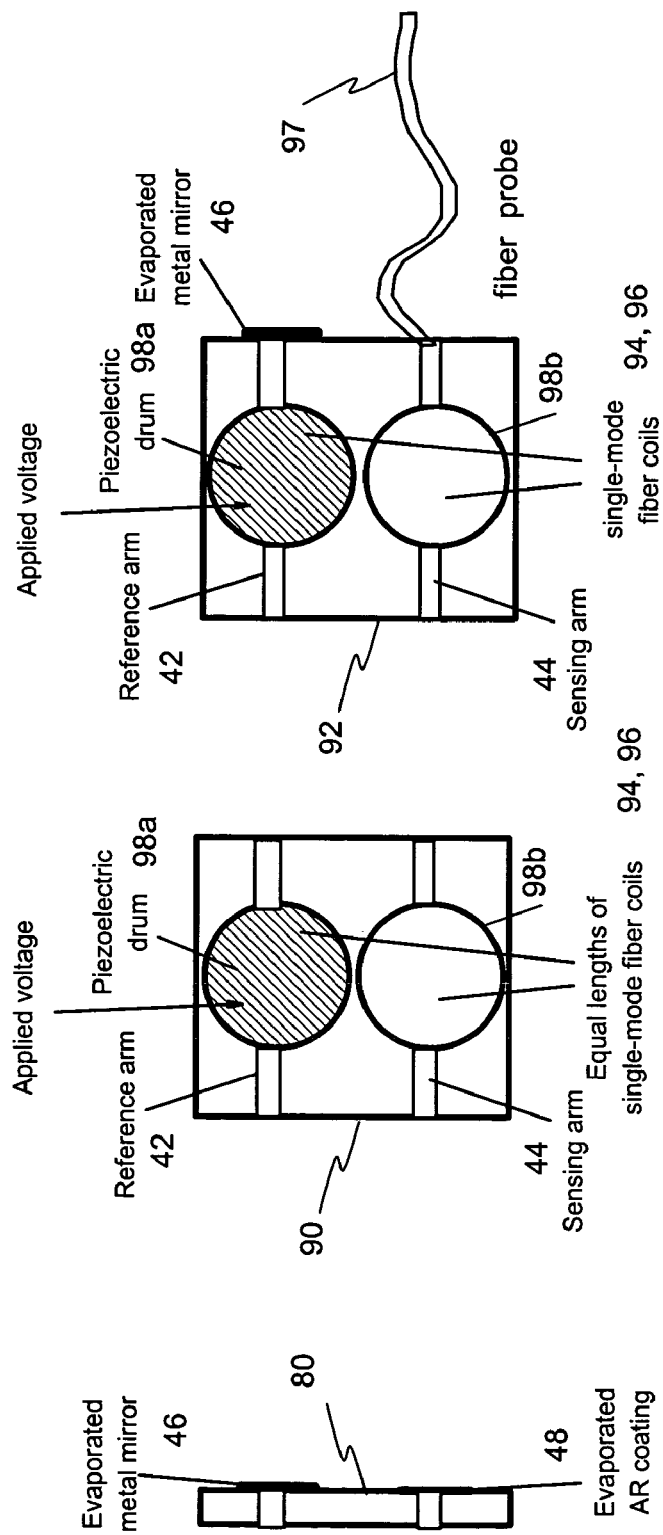
FIG. 14A depicts an interface for extension modules in accordance with another exemplary embodiment of the invention.
FIG. 14B depicts an interface for extension in accordance with another exemplary embodiment of the invention.
FIG. 14C depicts another interface for extension in accordance with yet another exemplary embodiment of the invention.

The configuration described above with reference to FIGS. 4A and 4B is convenient to use when the instrument can be placed directly in contact with the sample to provide a reading for a selected depth. Some applications may require the probing depth to be dynamic to enable locating a feature. For example, in medical diagnostics or imaging, the operator may need to probe for features such as tumors, characterized by large changes of optical properties (absorption, reflection, or refractive index change due to a different density). Some other (medical) applications may require a probe to be inserted into the body or object under study. For example, employing an expansion to the embodiments disclosed herein with a fiber probe with a catheter and guide wire to facilitate internal diagnostics and imaging. FIGS. 14A-14C depict an adapter and several expansion or extension modules 90, 92, which can be attached to the LCI system 10 of FIGS. 4A and 4B to provide additional versatility and functionality. FIG. 14A, depicts an adapter 80, configured, in one exemplary embodiment as a short section of waveguides 82, preferably, but not necessarily, made of the same material as the splitter-modulator 40a, 40b, with mirror 46 and AR coating 48, which can be attached to the splitter-modulator 40a, 40b (with matching fluid) to operate as an interface for various extension modules 90, 92. The purpose of the extension module 90 is to provide for adequate lengths of the reference and sensing arms 42, 44 while using a minimum of space, and for adjusting the length of the reference arm 42 and/or sensing arm 44 to enable probing at various depths. The length of the arms 42, 44 can be adjusted in any number of ways, including mechanically changing an air gap between two sections of the reference arm, moving the mirror 46, actually modifying the length of the arm, and the like, as well as combinations including at least one of the foregoing. A preferred way to manipulate the length of an arm 42, 44, in this instance the reference arm 42, in order to maintain small size, accuracy, and stability, is to perform this operation electromechanically.

Referring now to FIGS. 14B and 14C, in yet another exemplary embodiment, an extension modules 90 and 92 including windings of two lengths of single-mode fibers 94, 96, preferably a polarization maintaining fiber (PMF), (reference and sensing arms respectively) on two drums 98a and 98b. In one embodiment, the drum for the reference arm 42 is made out of a piezoelectric material such as, but not limited to PZT (lead zirconate titanate). The diameter of the drums is selected to be large enough to prevent radiation from the fibers 94, 96 due to the bending for example, about 3-4 centimeters (cm). The diameter of the fibers 94, 96 with claddings is of the order of 0.12 mm. The application of a voltage to the PZT drum 98a causes it to expand or contract, thus straining the reference fiber 94 (for example) and changing its effective length and thereby the optical path length for the reference arm 42. Therefore, as the total length of the unstrained fiber is increased, the total expansion increases as well. For example, if the strain limit for the fiber 94 is about $\Delta l/l$ is $10^{-4}$, then it requires a 10-meter length of fiber 94 to provide for about a 1 mm extension. Advantageously, a length tens of meters is relatively easy to achieve if the fiber 94 is not too lossy. In the 1.3 μm to 1.55 μm wavelength range, the absorption in optical fibers 94, 96 is of the order of 0.2 dB/Km. There for the losses associated with a 10 meter length would be quite small. Thus, the approach of using a voltage applied a piezoelectric drum e.g., 98a wound with a fiber 94 coil is an effective means to provide changes of several millimeters in the optical path length of the reference arm 42.

Continuing with FIGS. 14B and 14C, the extension module 90 is configured to provide the extension of the reference and sensing arms 42 and 44 as described above and interfaces with an adapter 80 to facilitate depth profiling. Extension module 92 also includes an evaporated metal mirror 46 to terminate the reference arm 42, while the sensing arm 44 is terminated with a fiber probe 97 configured to facilitate probing such as may include a guidewire and catheter.

Figure 15:
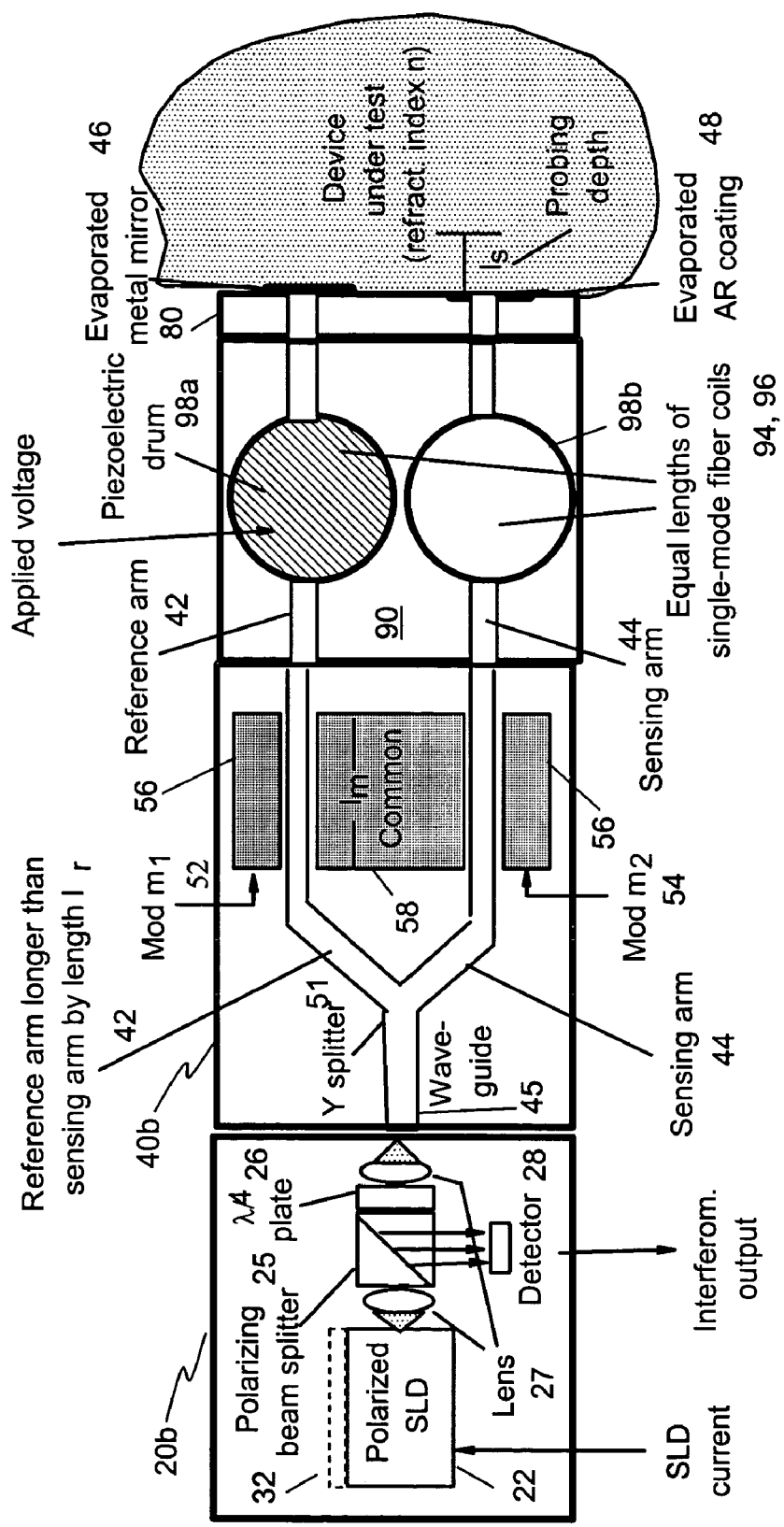
FIG. 15 depicts an adaptation of the interferometer system of FIGS. 4A and 4B for ranging measurements in accordance with another exemplary embodiment.
Figure 16:
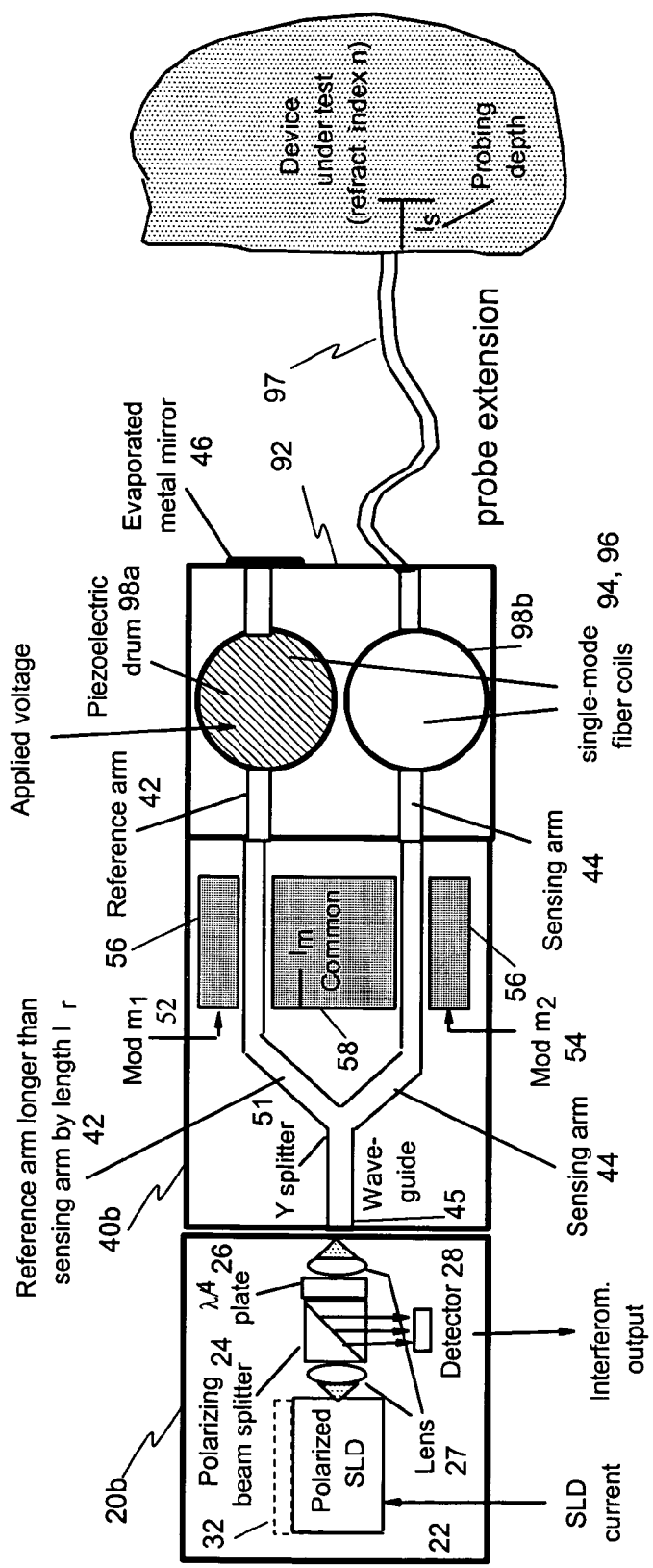
FIG. 16 depicts another adaptation of the interferometer system of FIGS. 4A and 4B for ranging measurements in accordance with yet another exemplary embodiment with external probe.

FIGS. 15 and 16 depict various implementations of the extended instrument starting from the base configuration depicted in FIGS. 4A and 4B and using the adapter and the extension modules 80, 90, and 92. FIG. 15 depicts a configuration of an exemplary embodiment where in addition to the source-detector module 20a, 20b and splitter modulator module 40a, 40b and extension module 90 and adapter 80 are employed. This configuration facilitates probing at various depths as well as facilitating depth profile scanning. FIG. 16 depicts a configuration of another exemplary embodiment where in addition to the source-detector module 20 and splitter modulator module 40 and extension module 92 including an external probe 97 are employed. This configuration facilitates probing either at a distance from the device or remote probing such as with a catheter and guidewire. FIG. 15 depicts a configuration of an exemplary embodiment where in addition to the source-detector module and splitter modulator module 40a, 40b and extension module 90 and adapter 80 are employed. This configuration facilitates probing at various depths as well as facilitating depth profile scanning.

The disclosed invention can be embodied in the form of computer, controller, or processor implemented processes and apparatuses for practicing those processes. The present invention can also be embodied in the form of computer program code containing instructions embodied in tangible media 66 such as floppy diskettes, CD-ROMs, hard drives, memory chips, or any other computer-readable storage medium, wherein, when the computer program code is loaded into and executed by a computer, controller, or processor 62, the computer, controller, or processor 62 becomes an apparatus for practicing the invention. The present invention may also be embodied in the form of computer program code as a data signal 68 for example, whether stored in a storage medium, loaded into and/or executed by a computer, controller, or processor 62 or transmitted over some transmission medium, such as over electrical wiring or cabling, through fiber optics, or via electromagnetic radiation, wherein, when the computer program code is loaded into and executed by a computer 62, the computer 62 becomes an apparatus for practicing the invention. When implemented on a general-purpose processor the computer program code segments configure the processor to create specific logic circuits.

It will be appreciated that the use of first and second or other similar nomenclature for denoting similar items is not intended to specify or imply any particular order unless otherwise stated.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for determining a characteristic of an analyte in a biological sample, the method comprising:
    directing broadband light by means of a sensing light path at the biological sample, at a target depth defined by said sensing light path and a reference light path;
    receiving said broadband light reflected from the biological sample by means of said sensing light path;
    directing said broadband light by means or said reference light path at a fixed reflecting device;
    receiving said broadband light reflected from said fixed reflecting device by means of said reference light path;
    modulating at about a distance of a center wavelength of said broadband light an effective light path length of at least one of said reference light path and said sensing light path with respect to said target depth;
    detecting said broadband light resulting from said broadband light reflected from said target depth in the biological sample and said broadband light reflected from said fixed reflecting device, to generate a signal indicative of an interference of said broadband light reflected from said target depth in the biological sample and said broadband light reflected from said fixed reflecting device, said signal having a phase component and an amplitude component, said amplitude component comprises an intensity measurement at said target depth;
    wherein said effective light path length of at least one of said reference light path and said sensing light path is modulated such that said phase component of said signal is sinusoidal and its magnitude generally proportional to said intensity measurement at said target depth;
    changing said effective light path length of at least one of said reference light path and said sensing light path to define an other target depth, said other target depth is at a distance of about at least a coherence length of said broadband light from said target depth;
    modulating at about a distance of the center wavelength of said broadband light said effective light path length of at least one of said reference light path and said sensing light path with respect to said other target depth;
    detecting said broadband light resulting from said broadband light reflected from said other target depth in the biological sample and said broadband light reflected from said fixed reflecting device, to generate an other signal indicative of an interference of said broadband light reflected from said other target depth in the biological sample and said broadband light reflected from said fixed reflecting device for said other target depth, said other signal having a phase component and an amplitude component, said amplitude component comprises an intensity measurement at said other target depth;
    wherein said effective light path length of at least one of said reference light path and said sensing light path is modulated such that said phase component of said other signal is sinusoidal and its magnitude generally proportional to said intensity measurement at said other target depth;
    determining the characteristic of the analyte in the biological sample from variations in said intensity measurements; and
    diagnosing a human condition from the characteristic.

2. The method of claim 1 wherein said determining the characteristic of the analyte in the biological sample from variations in said intensity measurements comprises:
    determining a scattering coefficient from said variations in said intensity measurements; and
    determining the characteristic of the analyte in the biological sample from said scattering coefficient.

3. The method of claim 1 wherein said target depth is defined by said effective light path length of said reference light path and said effective light path length of said sensing light path.

4. The method of claim 3 wherein said other target depth is defined by said effective light path length of at least one of said reference light path and said sensing light path having been changed.

5. The method of claim 1 wherein at least one of said reference light path and said sensing light path comprises at least one of an optical fiber and a waveguide.

6. The method of claim 1 wherein at least one of said modulating employs at least one metallic electrodes disposed at an optical waveguide and an optical fiber wound on a piezoelectric drum forming at least a portion of at least one of said reference light path and said sensing light path.

7. The method of claim 1 further including calibrating at least one of said reference light path and said sensing light path by adjusting effective light path length of at least one of said reference light path and said sensing light path based on a sample exhibiting properties including at least one of known refractive index and scattering coefficient.

8. A system for determining a characteristic of an analyte in a biological sample, the system comprising:
    a broadband light source for providing a broadband light;
    a sensing light path receptive to said broadband light from said broadband light source, said sensing light path configured to direct said broadband light at the biological sample and to receive said broadband light reflected from the biological sample;
    a fixed reflecting device;
    a reference light path receptive to said broadband light from said broadband light source, said reference light path configured to direct said broadband light at said fixed reflecting device and to receive said broadband light reflected from said fixed reflecting device, said reference light path and said sensing light path cooperating to define a target depth;
    means for modulating at about a distance of a center wavelength of said broadband light an effective light path length of at least one of said reference light path and said sensing light path with respect to said target depth;
    a detector receptive to said broadband light resulting from said broadband light reflected from said target depth in the biological sample and said broadband light reflected from said fixed reflecting device, to generate a signal indicative of an interference of said broadband light reflected from said target depth in the biological sample and said broadband light reflected from said fixed reflecting device, said signal having a phase component and an amplitude component, said amplitude component comprises an intensity measurement at said target depth;

wherein said means for modulating is such that said phase component of said signal is sinusoidal and its magnitude generally proportional to said intensity measurement at said target depth;

means for changing said effective light path length of at least one of said reference light path and said sensing light path to define an other target depth, said other target depth is at a distance of about at least a coherence length of said broadband light from said target depth;

wherein said means for modulating further modulates at about a distance of the center wavelength of said broadband light said effective light path length of at least one of said reference light path and said sensing light path with respect to said other target depth;

wherein said detector is further receptive to said broadband light resulting from said broadband light reflected from said other target depth in the biological sample and said broadband light reflected from said fixed reflecting device, to generate an other signal indicative of an interference of said broadband light reflected from said other target depth in the biological sample and said broadband light reflected from said fixed reflecting device, said other signal having a phase component and an amplitude component, said amplitude component comprises an intensity measurement at said other target depth;

wherein said means for modulating is such that said phase component of said other signal is sinusoidal and its magnitude generally proportional to said intensity measurement at said other target depth; and processing means configured to determine the characteristic of the analyte in the biological sample from variations in said intensity measurements.

9. The system of claim 8 wherein said processing means is further configured to determine a scattering coefficient from said variations in said intensity measurements and the characteristic of the analyte in the biological sample from said scattering coefficient.

10. The system of claim 8 wherein said effective light path length of said reference light path and said effective light path length of said sensing light path defines said target depth.

11. The system of claim 10 wherein said effective light path length of at least one of said reference light path and said sensing light path having been changed defines said other target depth.

12. The system of claim 8 wherein at least one of said reference light path and said sensing light path comprises at least one of an optical fiber and a waveguide.

13. The system of claim 8 wherein said means for modulating comprises metallic electrodes disposed at an optical waveguide and an optical fiber wound on a piezoelectric drum forming at least a portion of at least one of said reference light path and said sensing light path.

14. The system of claim 8 further including a calibrating strip for calibrating at least one of said reference light path and said sensing light path by adjusting effective light path length of at least one of said reference light path and said sensing light path based on a sample exhibiting properties including at least one of known refractive index and scattering coefficient.

15. A method for determining a characteristic of an analyte in a biological sample, die method comprising:

directing broadband light by means of a sensing light path at the biological sample, at a target depth defined by said sensing light path and a reference light path;

receiving said broadband light reflected from the biological sample by means of said sensing light path;

directing said broadband light by means of said reference light path at a fixed reflecting device;

receiving said broadband light reflected from said fixed reflecting device by means of said reference light path;

modulating at about a distance of a center wavelength of said broadband light an effective light path length of at least one of said reference light path and said sensing light path with respect to said target depth;

detecting said broadband light resulting from said broadband light reflected from said target depth in the biological sample and said broadband light reflected from said fixed reflecting device, to generate a signal indicative of an interference of said broadband light reflected from said target depth in the biological sample and said broadband light reflected from said fixed reflecting device, said signal having a phase component and an amplitude component, said amplitude component comprises an intensity measurement at said target depth;

wherein said effective light path length of at least one of said reference light path and said sensing light path is modulated such that said phase component of said signal is sinusoidal and its magnitude generally proportional to said intensity measurement at said target depth;

changing said effective light path length of at least one of said reference light path and said sensing light path to define an other target depth, said other target depth is at a distance of about at least a coherence length of the broadband light from said target depth;

modulating at about a distance of a center wavelength of said broadband light said effective light path length of at least one of said reference light path and said sensing light path with respect to said other target depth;

detecting said broadband light resulting from said broadband light reflected from said other target depth in the biological sample and said broadband light reflected from said fixed reflecting device, to generate an other signal indicative of an interference of said broadband light reflected from said other target depth in the biological sample and said broadband light reflected from said fixed reflecting device for said other target depth, said other signal having a phase component and an amplitude component, said amplitude component comprises an intensity measurement at said other target depth;

wherein said effective light path length of at least one of said reference light path and said sensing light path is modulated such that said phase component of said other signal is sinusoidal and its magnitude generally proportional to said intensity measurement at said other target depth;

determining a scattering coefficient from said variations in said intensity measurements; and determining the characteristic of the analyte in the biological sample from said scattering coefficient; and diagnosing a human condition from the characteristic.

16. The method of claim 15 wherein said target depth is defined by said effective light path length of said reference light path and said effective light path length of said sensing light path.

17. The method of claim 16 wherein said other target depth is defined by said effective light path length of at least one of said reference light path and said sensing light path having been changed.

18. The method of claim 15 wherein at least one of said reference light path and said sensing light path comprises at least one of an optical fiber and a waveguide.

19. The method of claim 15 wherein at least one of said modulating employs at least one metallic electrodes disposed at an optical waveguide and an optical fiber wound on a piezoelectric drum forming at least a portion of at least one of said reference light path and said sensing light path.

20. The method of claim 15 further including calibrating at least one of said reference light path and said sensing light path by adjusting effective light path length of at least one of said reference light path and said sensing light path based on a sample exhibiting properties including at least one of known refractive index and scattering coefficient.

21. A system for determining a characteristic of an analyte in a biological sample, the system comprising:
a broadband light source for providing a broadband light;
a sensing light path receptive to said broadband light from said broadband light source, said sensing light path configured to direct said broadband light at the biological sample and to receive said broadband light reflected from the biological sample;
a fixed reflecting device;
a reference light path receptive to said broadband light from said broadband light source, said reference light path configured to direct said broadband light at said fixed reflecting device and to receive said broadband light reflected from said fixed reflecting device, said reference light path and said sensing light path cooperating to define a target depth;
means for modulating at about a distance of a center wavelength of said broadband light an effective light path length of at least one of said reference light path and said sensing light path with respect to said target depth;
a detector receptive to said broadband light resulting from said broadband light reflected from said target depth in the biological sample and said broadband light reflected from said fixed reflecting device, to generate a signal indicative of an interference of said broadband light reflected from said target depth in the biological sample and said broadband light reflected from said fixed reflecting device, said signal having a phase component and an amplitude component, said amplitude component comprises an intensity measurement at said target depth;
wherein said means for modulating is such that said phase component of said signal is sinusoidal and its magnitude generally proportional to said intensity measurement at said target depth;
means for changing said effective light path length of at least one of said reference light path and said sensing light path to define an other target depth, said other target depth is at a distance of about at least a coherence length of the broadband light from said target depth;
wherein said means for modulating further modulates said effective light path length of at least one of said reference light path and said sensing light path with respect to said other target depth;
wherein said detector is further receptive to said broadband light resulting from said broadband light reflected from said other target depth in the biological sample and said broadband light reflected from said fixed reflecting device, to generate an other signal indicative of an interference of said broadband light reflected from said other target depth in the biological sample and said broadband light reflected from said fixed reflecting device, said other signal having a phase component and an amplitude component, said amplitude component comprises an intensity measurement at said other target depth;
wherein said means for modulating is such that said phase component of said other signal is sinusoidal and its magnitude generally proportional to said intensity measurement at said other target depth; and
processing means configured to determine a scattering coefficient from said variations in said intensity measurements and the characteristic of the analyte in the biological sample from said scattering coefficient.

22. The system of claim 21 wherein said effective light path length of said reference light path and said effective light path length of said sensing light path defines said target depth.

23. The system of claim 22 wherein said effective light path length of at least one of said reference light path and said sensing light path having been changed defines said other target depth.

24. The system of claim 21 wherein at least one of said reference light path and said sensing light path comprises at least one of an optical fiber and a waveguide.

25. The system of claim 21 wherein said means for modulating comprises metallic electrodes disposed at an optical waveguide and an optical fiber wound on a piezoelectric drum forming at least a portion of at least one of said reference light path and said sensing light path.

26. The system of claim 21 further including a calibrating strip for calibrating at least one of said reference light path and said sensing light path by adjusting effective light path length of at least one of said reference light path and said sensing light path based on a sample exhibiting properties including at least one of known refractive index and scattering coefficient.

27. A method for determining a characteristic of an analyte in a biological sample, the method comprising:
directing broadband light by means of a sensing light path at the biological sample, at a target depth defined by said sensing light path and a reference light path;
receiving said broadband light reflected from the biological sample by means of said sensing light path;
directing said broadband light by means of said reference light path at a fixed reflecting device;
receiving said broadband light reflected from said fixed reflecting device by means of said reference light path;
modulating at about a distance of a center wavelength of said broadband light an effective light path length of at least one of said reference light path and said sensing light path with respect to said target depth;
detecting said broadband light resulting from said broadband light reflected from said target depth in the biological sample and said broadband light reflected from said fixed reflecting device, to generate a signal indicative of an interference of said broadband light reflected from said target depth in the biological sample and said broadband light reflected from said fixed reflecting device, said signal having a phase component and an amplitude component, said amplitude component comprises an intensity measurement at said target depth;

wherein said effective light path length of at least one of said reference light path and said sensing light path is modulated such that said phase component of said signal is sinusoidal and its magnitude generally proportional to said intensity measurement at said target depth;

changing said effective light path length of at roast one of said reference light path and said sensing light path to define an other target depth, said other target depth is at a distance of about at least a coherence length of the broadband light from said target depth;

modulating at about a distance of a center wavelength of said broadband light said effective light path length of at least one of said reference light path and said sensing light path with respect to said other target depth;

detecting said broadband light resulting from said broadband light reflected from said other target depth in the biological sample and said broadband light reflected from said fixed reflecting device, to generate an other signal indicative of an interference of said broadband light reflected from said other target depth in the biological sample and said broadband light reflected from said fixed reflecting device for said other target depth, said other signal having a phase component and an amplitude component, said amplitude component comprises an intensity measurement at said other target depth;

wherein said effective light path length of at least one of said reference light path and said sensing light path is modulated such that said phase component of said other signal is sinusoidal and its magnitude generally proportional to said intensity measurement at said other target depth;

determining the characteristic of the analyte in the biological sample from variations in said intensity measurements; and calibrating at least one of said reference light path and said sensing light path by adjusting effective light path length of at least one of said reference light path and said sensing light path based on a sample exhibiting properties including at least one of known refractive index and scattering coefficient.

28. The method of claim 27 wherein said target depth is defined by said effective light path length of said reference light path and said effective light path length of said sensing light path.

29. The method of claim 28 wherein said other target depth is defined by said effective light path length of at least one of said reference light path and said sensing light path having been changed.

30. The method of claim 27 wherein at least one of said reference light path and said sensing light path comprises at least one of an optical fiber and a waveguide.

31. The method of claim 27 wherein at least one of said modulating employs at least one metallic electrodes disposed at an optical waveguide and an optical fiber wound on a piezoelectric drum forming at least a portion of at least one of said reference light path and said sensing light path.

32. A system for determining a characteristic of an analyte in a biological sample, the system comprising:

a broadband light source for providing a broadband light;

a sensing light path receptive to said broadband light from said broadband light source, said sensing light path configured to direct said broadband light at the biological sample and to receive said broadband light reflected from the biological sample;

a fixed reflecting device;

a reference light path receptive to said broadband light from said broadband light source, said reference light path configured to direct said broadband light at said fixed reflecting device and to receive said broadband light reflected from said fixed reflecting device, said reference light path and said sensing light path cooperating to define a target depth;

means for modulating at about a distance of a center wavelength of said broadband light an effective light path length of at least one of said reference light path and said sensing light path with respect to said target depth;

a detector receptive to said broadband light resulting from said broadband light reflected from said target depth in the biological sample and said broadband light reflected from said fixed reflecting device, to generate a signal indicative of an interference of said broadband light reflected from said target depth in the biological sample and said broadband light reflected from said fixed reflecting device, said signal having a phase component and an amplitude component, said amplitude component comprises an intensity measurement at said target depth;

wherein said means for modulating is such that said phase component of said signal is sinusoidal and its magnitude generally proportional to said intensity measurement at said target depth;

means for changing said effective light path length of at least one of said reference light path and said sensing light path to define an other target depth, said other target depth is at a distance of about at least a coherence length of the broadband light from said target depth;

wherein said means for modulating further modulates said effective light path length of at least one of said reference light path and said sensing light path with respect to said other target depth;

wherein said detector is further receptive to said broadband light resulting from said broadband light reflected from said other target depth in the biological sample and said broadband light reflected from said fixed reflecting device, to generate an other signal indicative of an interference of said broadband light reflected from said other target depth in the biological sample and said broadband light reflected from said fixed reflecting device, said other signal having a phase component and an amplitude component, said amplitude component comprises an intensity measurement at said other target depth;

wherein said means for modulating is such that said phase component of said other signal is sinusoidal and its magnitude generally proportional to said intensity measurement at said other target depth; and processing means configured to determine the characteristic of the analyte in the biological sample from variations in said intensity measurements; and a calibrating strip for calibrating at least one of said reference light path and said sensing light path by adjusting effective light path length of at least one of said reference light path and said sensing light path based on a sample exhibiting properties including at least one of known refractive index and scattering coefficient.

33. The system of claim 32 wherein said effective light path length of said reference light path and said effective light path length of said sensing light path defines said target depth.

34. The system of claim 33 wherein said effective light path length of at least one of said reference light path and said sensing light path having been changed defines said other target depth.

35. The system of claim 32 wherein at least one of said reference light path and said sensing light path comprises at least one of an optical fiber and a waveguide.

36. The system of claim 32 wherein said means for modulating comprises metallic electrodes disposed at an optical waveguide and an optical fiber wound on a piezoelectric drum forming at least a portion of at least one of said reference light path and said sensing light path.

* * * * *